(12) United States Patent
Larsen et al.

(10) Patent No.: US 7,521,193 B2
(45) Date of Patent: Apr. 21, 2009

(54) HUMAN DIABETES-MEDIATING PROTEINS

(75) Inventors: Peter Mose Larsen, Odense (DK); Stephen J. Fey, Aarhus (DK); Jørn Nerup, Holte (DK); Allan E. Karlsen, Allerød (DK)

(73) Assignee: Pride Proteomics A/S, Odense M (DK)

( * ) Notice: Subject to any disclaimer, the term of this patent is extended or adjusted under 35 U.S.C. 154(b) by 63 days.

(21) Appl. No.: 10/508,255

(22) PCT Filed: Mar. 20, 2003

(86) PCT No.: PCT/DK03/00190

§ 371 (c)(1), (2), (4) Date: Sep. 30, 2005

(87) PCT Pub. No.: WO03/078456

PCT Pub. Date: Sep. 25, 2003

(65) Prior Publication Data

US 2006/0073134 A1  Apr. 6, 2006

(30) Foreign Application Priority Data

Mar. 20, 2002 (DK) .............................. 2002 00431

(51) Int. Cl.
*G01N 33/53* (2006.01)
*C07K 14/00* (2006.01)

(52) U.S. Cl. ........................................ 435/7.1; 530/350
(58) Field of Classification Search .................. 435/7.1; 530/350

See application file for complete search history.

(56) References Cited

FOREIGN PATENT DOCUMENTS

WO  WO 98 20124 A  5/1998

OTHER PUBLICATIONS

Christofilis et al. 1999; Serum reg protein level is not related to beta cell destruction/regeneration process during early phases of diabetogenesis in type I diabetes. European Journal of Endocrinology 141: 368-373.*
Baeza et al. 1996a. Pancreatic regenerating gene overexpression in the nonobese diabetic mouse during active diabetogenesis. Diabetes. 45:67-70.*
Baeza et al. 1996b. Reg protein: A potential beta-cell-specific growth factor? Diabetes & Metabolism 22: 229-234.*
Ishii et al. 1993; Appearance of a regerating (reg) gene protein in pancreatic islets of remission BB/Wor/Tky rats. Endocrine Journal/ 40(2): 269-273.*
DeReggi et al. 2001; Protein-X, pancreatic stone-, pancreatic thread-reg-protein, P19, lithostathine, and now what? Current Protein and Peptide Science. 2: 19-42.*
Wang et al. 2007; Lipocalin-2 is an inflammatory marker closely associated with obesity, insulin resistance, and hyperglycemia in humans. Clinical Chemistry. 53(1): 34-41.*
International Search Report, Oct. 29, 2003.

* cited by examiner

*Primary Examiner*—Karen Cochrane Carlson
(74) *Attorney, Agent, or Firm*—Stephen A. Bent; Foley & Lardner LLP

(57) ABSTRACT

Determining the expression level of certain diabetes-mediating proteins provides an approach both for diagnosing diabetes and for ascertaining a predisposition for developing diabetes.

4 Claims, 3 Drawing Sheets

HUMAN DIABETES-MEDIATING PROTEINS

RELATED APPLICATIONS

Figure 1:
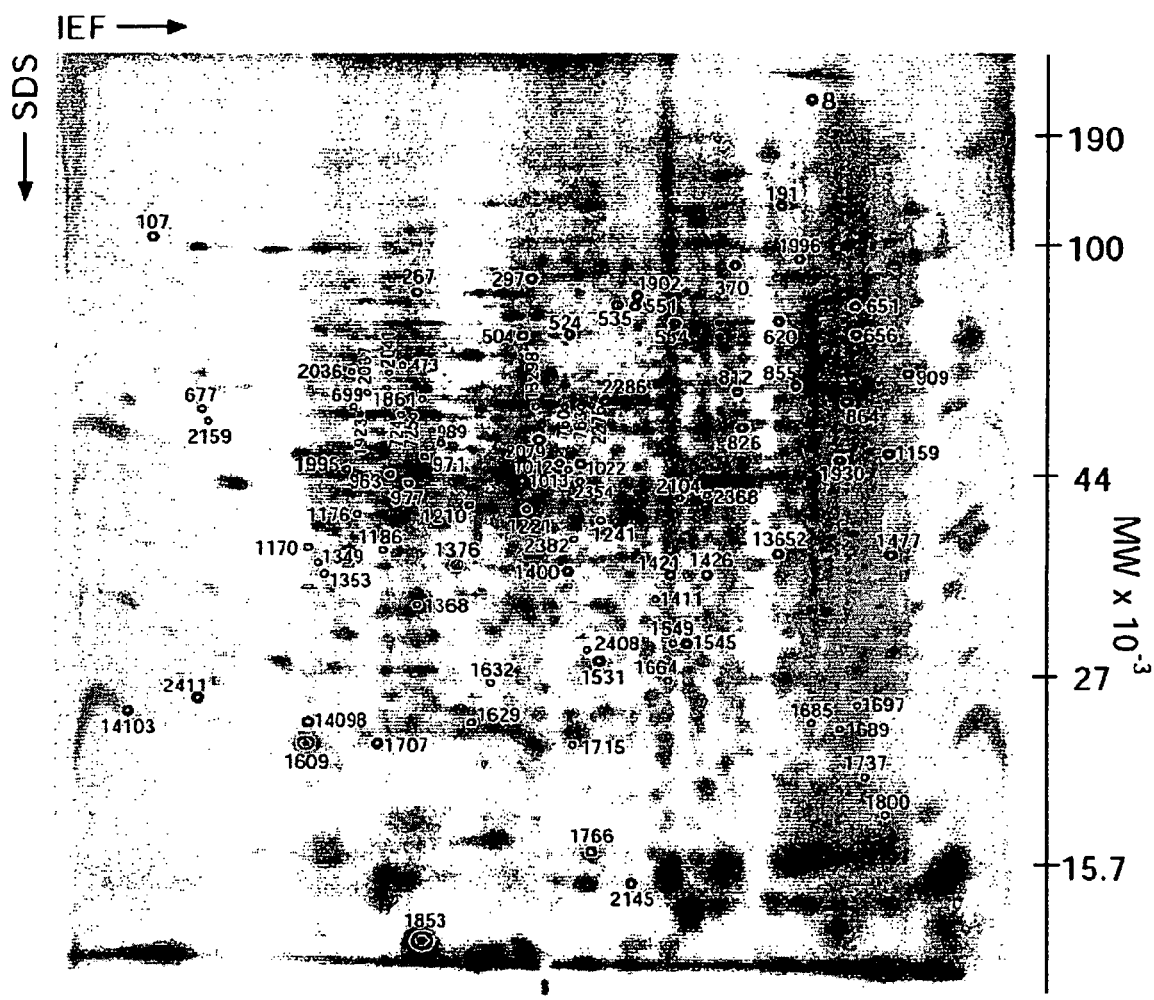

This application is the U.S. National Phase of PCT/DK03/00190 filed Mar. 20, 2003 which claims priority from Danish Patent Application No. PA 2002 00431 filed on Mar. 20, 2002, each of which is incorporated herein by reference in its entirety.

FIELD OF THE INVENTION

This invention relates generally to human diabetes-mediating proteins, methods of identifying diabetes-mediating proteins, methods for screening for drugs which affect the expression of diabetes-mediating proteins, and therapeutic compounds for the treatment and prevention of diabetes.

BACKGROUND OF THE INVENTION

The development of insulin-dependent diabetes mellitus (IDDM) in man, and in animal models of human disease, is characterised by mononuclear cell infiltration and β cell destruction in the pancreatic islets (insulitis). The mechanisms behind β-cell destruction is not known. Accumulating evidence indicates that the cytokines like interleukin-1β (IL-1β), tumour necrosis factor α (TNF-α) or interferon-γ (IFN-γ) or combinations of them, primarily produced by macrophages and monocytes, may be a mediator of islet β-cell destruction [Mandrup-Poulsen T, Nerup J. *New concepts in the pathogenesis of insulin-dependent diabetes mellitus.* Contrib Nephrol. 1989; 73:1-14; discussion 14-5].

Animal models of human diabetes include diabetes-prone BB (BB-DP) rats and non-obese diabetic (NOD) mice. 2-Dimensional (2D) gel maps of rat islet proteins have been constructed and used to determine qualitative and quantitative changes in protein synthesis resulting with in vitro exposure of rat islet cells to IL-1β (Andersen et al. (1995) Diabetes 44:400-407; John N E et al., Diabetes. (2000); 49:1819-29. Christensen et al., Autoimmunity. (2000); 32:1-15 and Mose Larsen et al., Diabetes. (2001); 50:1056-63). PCT/IB97/01627 describes diabetes-mediating proteins identified by 2-dimensional gel analysis from rats.

SUMMARY OF THE INVENTION

The invention is based, in part, on the discovery and identification of human diabetes-mediating (DM) proteins. DM proteins are proteins which are involved in the development of diabetes or in the prevention of diabetes development in a subject at risk for the development of diabetes, and are identified by differential expression during the presence and absence of disease development. The development of diabetes includes all stages which precede the clinically detectable stage.

Accordingly, in one aspect the invention features substantially purified human protein, wherein the protein is present in a human islet cell and exhibits an altered expression during the development of diabetes relative to expression in the absence of diabetes development. The purified diabetes-mediating proteins of the invention are selected from the proteins listed in the Tables (including all modifications (such as biochemically or chemically modified proteins), variants or degradation products thereof), and especially in the Tables 6, 7, and 8. In a related aspect, the invention features an isolated protein selected from the group consisting of IEF spots 8, 370, 473, 524, 535, 551, 651, 656, 909, 1013, 1186, 1353, 1400, 1477, 1549, 1629, 1685, 1689, 1707, 1715, 1766, 1800, 1902, 1935, 2041, 2079, 2354, 2382, 2408, 2411, 13652, and 14098 (as listed in Table 6), NEPHGE spots 26, 35, 60, 76, 85, 128, 130, 171, 187, 188, 195, 243, 270, 421, 449, 508, 509, 532, 558, 560, 609, 719, 729, 829, 836, 837, 3879, and 6600 (as listed in Table 7) and IEF spots 122SPI, 123SPI, 126SPI, 130SPI, 135SPI, 140SPI, 160SPI, 218SPI, 248SPI, 277SPI, 304SPI, 314SPI, and 338SPI (as listed in Table 8). The expression of one or more of these proteins (including all modifications, variants or degradation products thereof) may be used to estimate the risk of a test subject for the development of diabetes by obtaining a biological sample from the test subject, and determining the level of expression of one or more of the above listed proteins, wherein an altered expression of one or more of the above-listed proteins may indicate risk of disease development.

In another aspect, the invention features a database of human islet cell proteins, which proteins are identified as human islet cell proteins exhibiting altered protein expression when exposed to a combination of one or more cytokines, relative to a non-exposed human islet cells. In one embodiment, the cells are exposed to IL-1β; in another embodiment, the cells are exposed to a mixture of cytokines comprising one of (i) IFNγ and TNFα, (ii) IFNγ and TNFα, and (iii) IL-1β, IFNγ, and TNFα. In a specific embodiment, a database of human diabetes-mediating proteins is generated by exposure of cells to a combination of IL-1β, IFNγ, and TNFα. In a more specific embodiment, the invention features a database of proteins identified as human islet cell proteins exhibiting altered expression when human islet cells are exposed to 150 pg/ml IL-1β, 1000 U/ml IFNγ, and 5000 U/ml TNFα. This is referred to as 'cytokine mix' throughout this document and in the tables.

Figure 2:
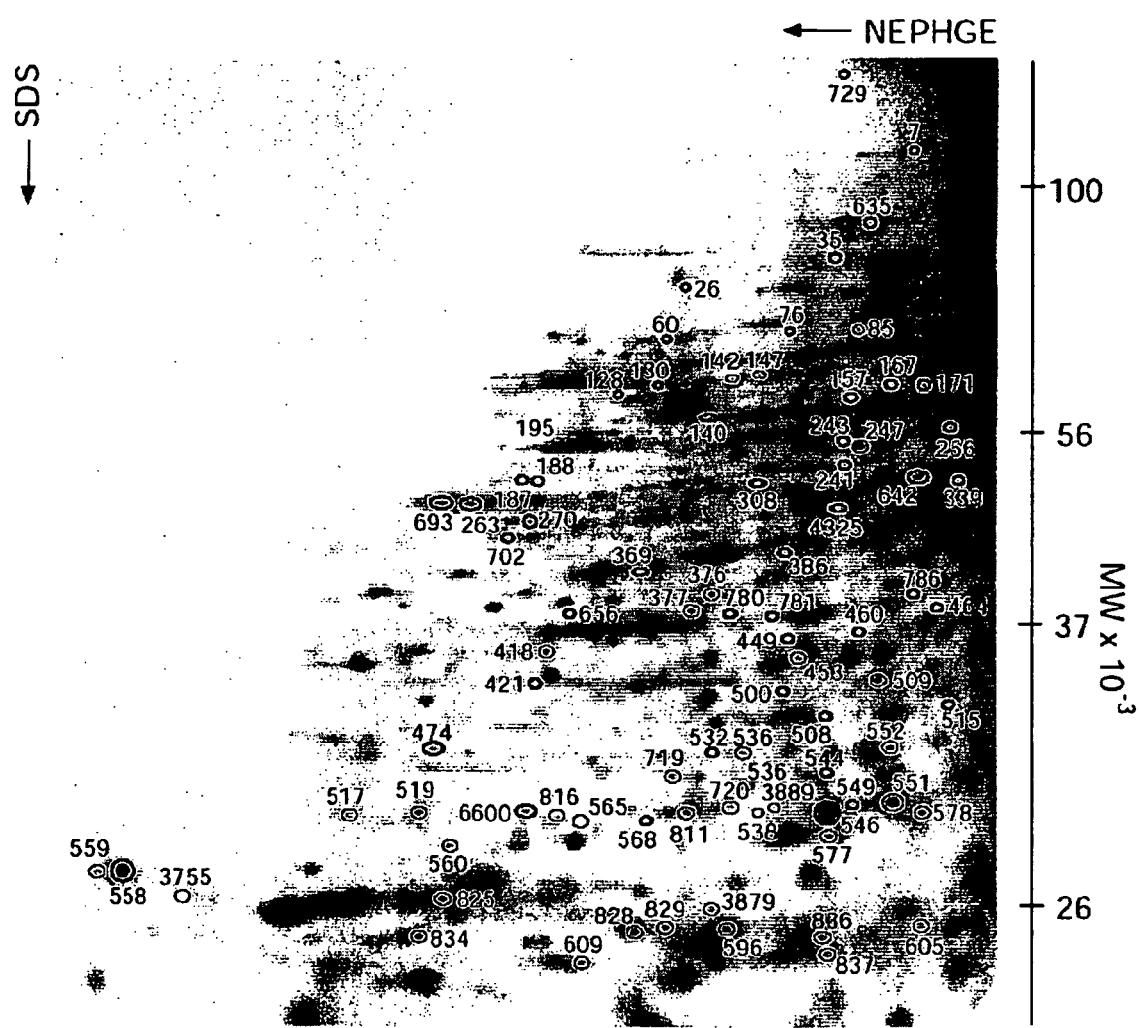
Figure 3:
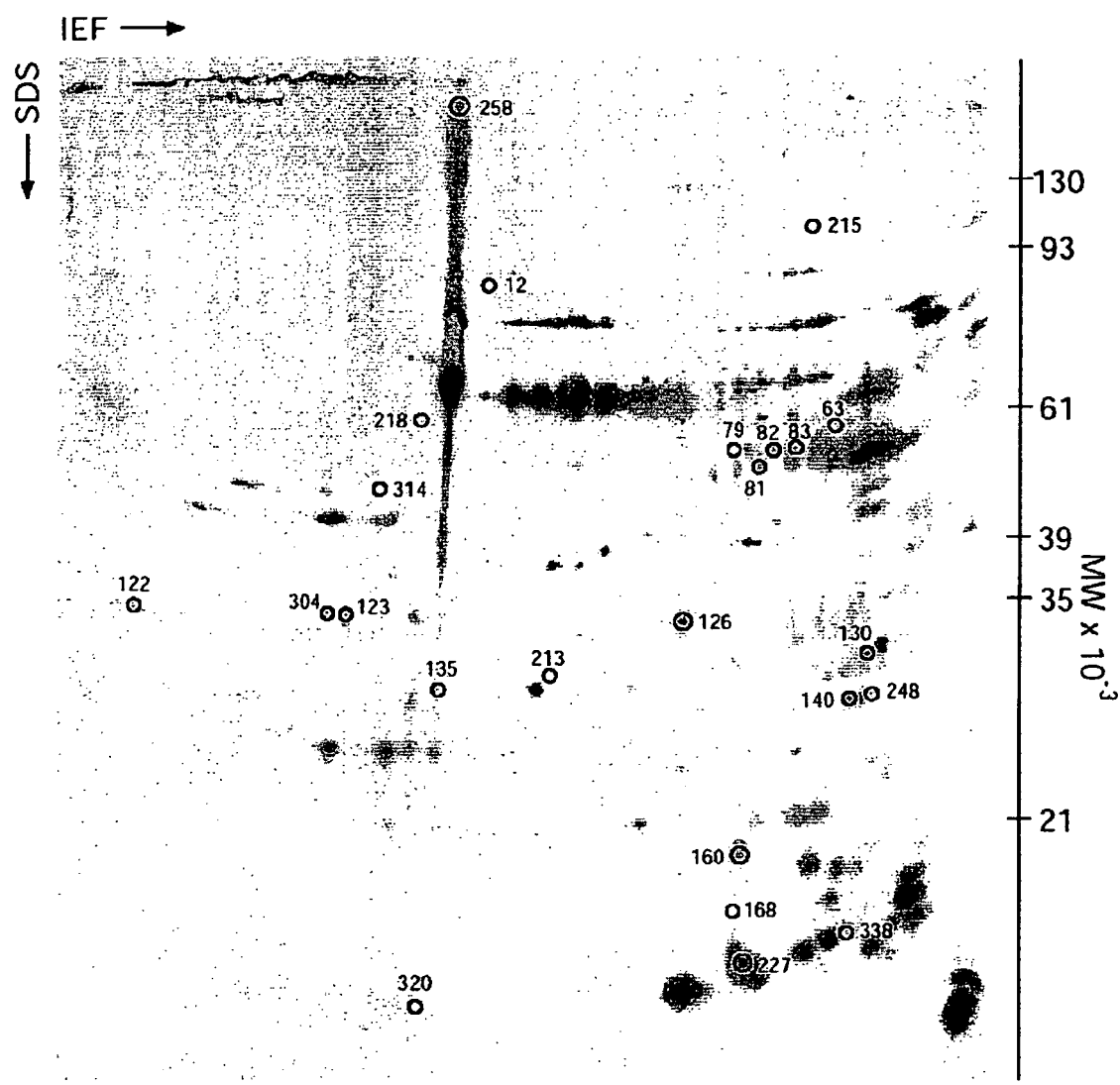

Proteins exhibiting an altered expression relative to control cells comprise the database of the proteins listed in Tables 1, 2 and 3 and shown in FIGS. 1, 2 and 3. In more specific embodiments, the invention provides subsets of proteins from the protein database comprising the proteins listed in Tables 1, 2 and 3. The database subsets include marker proteins that are diagnostically useful for predicting and/or assessing the risk of a subject for development of diabetes. Accordingly, in one aspect, the invention provides a subset of marker proteins selected from the proteins listed in Table 1 and/or Table 2 and/or Table 3 including all their variants, post-translational modifications, degradation products and peptides derived there from and homologous proteins. In a more specific embodiment, the database comprises 5 or more, 10 or more, 15 or more, or 25 or more of the proteins listed in Table 1, Table 2 and Table 3.

In a related aspect, the invention features a database of secreted human islet cell proteins, comprising secreted human islet cell proteins exhibiting altered expression when exposed to IL-1β, IFNγ, and TNFα, relative to a non-exposed human islet cells. In a specific embodiment, the protein database is comprised of the proteins listed in Table 3 and shown in FIG. 3. These proteins include the proteins identified as 12SPI, 63SPI, 79SPI, 81SPI, 82SPI, 83SPI, 122SPI, 123SPI, 126SPI, 130SPI, 135SPI, 140SPI, 160SPI, 168SPI, 213SPI, 215SPI, 215SPI, 218SPI, 248SPI, 258SPI, 258SPI, 259SPI, 277SPI, 304SPI, 314SPI, 320SPI, 338SPI, and 1157SPI. In more specific embodiments, the database comprises a subpopulation of the secreted proteins listed in Table 3. In even more specific embodiments, the database comprises 15 or more, 10 or more, and 5 or more of said proteins.

In another related aspect, the combinations of proteins may be between the cellular proteins (listed in Tables 1 and 2) and the secreted proteins (listed in Table 3).

As shown in Tables 1, 2 and 3 and FIGS. 1, 2 and 3, a number of the diabetes-mediating proteins are identified by correspondence to previously identified proteins by mass spectrometry. Proteins not corresponding to previously identified proteins are characterized herein by their mass spectroscopy spectrum. Novel non-secreted human diabetes-mediating proteins characterized by molecular weight, pI, and the mass spectroscopic characteristics are further grouped in Table 6 for proteins identified on IEF gels, and in Table 7 for proteins identified on NEPHGE gels. For some proteins it was not possible to obtain a mass spectrum and so they are only characterised by their isoelectric point and molecular weight and position in the gel electrophoretograms (FIGS. 1, 2 and 3).

As shown in Table 3 for secreted diabetes-mediating proteins, a number of the secreted diabetes-mediating proteins are identified by correspondence to previously identified proteins by correspondence of pI and molecular weight. Novel secreted proteins, that is proteins not corresponding to previously identified proteins, are characterized herein by mass spectroscopy spectrum (Table 8).

The diabetes-mediating proteins of the invention are useful in drug screening assays for identifying compounds capable of modulating the development of diabetes, useful as therapeutic agents for the treatment or prevention of diabetes, and useful as targets of therapeutic agents capable of preventing or ameliorating diabetes by modulating the expression of the diabetes-mediating protein.

Changes in the expression of specific DM proteins are diagnostically useful as indicative of the development of diabetes and for predicting the course of its development (prognosis). Accordingly, in one aspect the invention features a method for diagnosing the development of diabetes by measuring an increase or a decrease in protein expression in one or more proteins selected from the group consisting of the non-secreted and/or secreted diabetes-mediating proteins listed in Tables 1-3. Changes in protein expression are measured in a test subject suspected of developing diabetes or at risk for the development of diabetes and are expressed relative to protein expression in a normal non-diabetes control. In a preferred embodiment, changes of combinations of one or more of the proteins of Tables 1-3 is indicative of the development of diabetes. In a more preferred embodiment, changes of a combination of at least 5 of the proteins of Tables 1-3 is indicative of the development of diabetes. In an even more preferred embodiment, changes of a combination of at least 10 of the proteins of Tables 1-3 is indicative of the development of diabetes.

The invention provides identified diabetes-mediating proteins which may be further characterized as protective or deleterious proteins, as described in PCT/IB97/01627, the text of which application is specifically incorporated herein by reference. A protective protein is one which prevents, inhibits, or slows the development of diabetes in a subject at risk for diabetes, and a deleterious protein is one that causes the development of diabetes, increases the risk of development of diabetes, or decreases the time required for the development of diabetes in a subject at risk for developing diabetes. A deleterious protein is also a protein that prevents or interferes with the expression of a protective protein.

The invention includes a substantially purified protective or deleterious diabetes-mediating protein, and polynucleotide sequence which encodes the diabetes-mediating protein of the invention.

In one aspect, the invention features an assay for screening compounds which effect the expression of one or more diabetes-mediating proteins. In specific embodiments, the invention provides an assay for identifying a compound capable of inducing or enhancing the expression of an endogenous protective protein, and thus to delay or inhibit the development of diabetes. In another specific embodiment, the assay method of the invention is useful for identifying a compound capable of suppressing or inhibiting the expression of a deleterious diabetes-mediating protein, thus delaying or inhibiting the development of diabetes.

In a related aspect, the invention provides an assay for identifying a compound which modulates the activity of a diabetes-mediating protein, e.g., an agonist, an antagonist, or by blocking a post-translational step required for activation of a diabetes-mediating protein. Changes in the expression of specific DM proteins are useful in a screening method for identifying compounds capable of modulate the expression of DM proteins. A compound which modulates the expression of one or more diabetes mediating proteins is useful as a potential therapeutic in the treatment or prevention of diabetes. Accordingly, in one aspect the invention features an assay method for identifying compounds capable of modulating the expression of diabetes-mediating proteins having the steps of contacting a test compound with a cell or tissue expressing one or more diabetes-mediating proteins, and determining the effect of the test compound on the expression of one or more diabetes-mediating proteins. Determination of the effect of a compound may be conducted by a variety of methods known to the art, including hybridization to probes or other oligonucleotides, antibody recognition, e.g., immunodiffusion, immunofluorescence, ELISA, RIA, blotting, immunoprecipitation, immunoelectrophoresis, or chromatography, and electrophoresis. A compound capable of increasing the expression of one or more proteins selected from the group consisting of the diabetes-mediating proteins listed in Tables 1, 2 and 3 and decreasing the expression of one or more proteins selected from the list consisting of the diabetes-mediating proteins listed in Tables 1, 2 and 3 is a candidate therapeutic agent for the prevention or treatment of diabetes. Changes in protein expression are determined relative to expression in the absence of the test compound.

In another aspect, the invention provides a therapeutic method for preventing diabetes in a subject at risk for diabetes or of ameliorating the symptoms of diabetes in a diabetic subject by administering a therapeutically effective amount of a protective diabetes-mediating protein. Preferably the subject is a human. Also included in the invention is gene therapy by providing a polynucleotide encoding a protective diabetes-mediating protein. The invention further includes a therapeutic method for preventing and/or treating diabetes by administering an effective amount of a polynucleotide which inhibits the in vivo expression of a deleterious diabetes-mediating protein. Candidate therapeutic compounds are selected from the proteins of Tables 1, 2, and 3, homologues and derivatives thereof and mimics thereof.

In a related aspect, the invention provides a therapeutic method of preventing and/or treating diabetes in a subject at risk for diabetes by administering a therapeutically effective amount of a compound capable of suppressing or reducing the expression of an endogenous deleterious diabetes-mediating protein. In another embodiment, the invention provides a therapeutic method of preventing and/or treating diabetes by administering a therapeutically effective amount of a compound capable of inducing or enhancing the expression of an endogenous protective diabetes-mediating protein. In a related aspect, the invention provides a therapeutic method of preventing and/or treating diabetes in a subject at risk for diabetes by administering a therapeutically effective amount of a compound capable of modulating the activity of a diabetes-mediating protein, e.g., as an agonist, an antagonist, or by preventing the activation of a diabetes-mediating protein. The therapeutic method of the invention includes ex vivo methods known to the art for providing the therapeutic agent to a subject in need thereof.

An object of the invention is to identify human proteins which mediate diabetes onset.

Another object of the invention is to provide human diabetes-mediating proteins which are useful in assays for identifying test compounds capable of preventing, delaying, or ameliorating diabetes in a subject.

Another object of the invention is to provide human diabetes-mediating proteins which are useful in assays for identifying test compounds capable of causing, accelerating or worsening diabetes in a subject, indicating that the test compound would not be suitable as a pharmaceutical compound.

These and other objects, advantages, and features of the invention will become apparent to those persons skilled in the art upon reading the details of the diabetes-mediating gene(s) and protein(s), assay method and from the claims.

DETAILED DISCLOSURE OF THE INVENTION

A first aspect of the invention relates to a method for diagnosing diabetes in a human, the method comprising determining the presence or level of expression of at least one marker protein in a biological sample from the human, wherein the marker protein is selected from the group consisting of any one of the proteins disclosed in Tables 1, 2 and 3, and FIGS. 1, 2, and 3 and marker proteins which are modifications and derivatives of marker proteins of Table 1, 2 or 3, so as to have at least 80% homology with marker proteins of Table 1, 2 or 3, wherein pI is the isoelectric point of the marker protein as determined by isoelectric focusing, an up-arrow means that the protein is up-regulated in exposed cells, a down-arrow means that the protein is down-regulated in exposed cells and the molecular weight (Mol. Wt in kDa) is determined on a polyacrylamide gel.

Furthermore, the applications of the method comprises preferably at least 2, at least 5, or even more preferably at least 10 of said proteins because the modification in expression of 2 or more, 5 or more or 10 or more are increasingly statistically-reliable indicators for the application of these markers.

A further aspect relates to a method for diagnosing diabetes in a human, the method comprising determining the presence or level of expression of at least one marker protein in a biological sample from the human, an further comprising establishing the increased expression of at least one marker protein (an up-regulated marker protein) or establishing the decreased expression of at least one marker protein (a down-regulated marker protein) selected from the group consisting of proteins or combinations of up- and down-regulated marker proteins.

The invention further relates to a method of treating diabetes by the up-regulation of a down-regulated protein, the down-regulation of an up-regulated protein, or combinations thereof. That is to say that the invention relates to a method of treating diabetes in a human comprising altering the expressing of a marker protein of Table 1, 2 or 3 shown also in FIGS. 1, 2 and 3. Furthermore, the invention relates to method of treating diabetes in a human comprising administering a marker protein of Table 1, 2 or 3, a nucleotide sequence coding for a marker protein of Table 1, 2 or 3, an antibody for a protein of Table 1, 2 or 3, a nucleic acid fragment capable of binding to a marker protein of Table 1, 2 or 3, or a compound capable of binding to a marker protein of Table 1, 2 or 3 to said human.

In the course of identifying marker proteins as marker proteins for diabetes, said marker proteins either previously not known to be associated with diabetes or their level of expression not known in diabetes (down- or up-regulated), the present investigators have now isolated proteins previously not identified, and certainly not associated with diabetes. In connection to these novel proteins, the invention further relates to a protein selected from the group consisting of proteins of Table 1, 2 and 3 and proteins with at least 80% homology therewith.

A further aspect relates to the use of novel proteins and proteins of Table 1, 2 and 3 as markers or indicators for diabetes as well as to the use of known proteins whose presence, absence or prevalence has previously not been associated with diabetes. The changes in protein expression and patterns of protein expression are considered to be important markers for diagnosis, prognosis and therapeutic applications and targets.

The method of the present invention may be further used to determine the predisposition in a human for diabetes, the method comprising determining the presence or relative level in a biological sample from the human of at least one marker protein wherein the marker protein being indicative of a predisposition for having diabetes is selected from the group consisting of the proteins disclosed in the tables 1, 2 and 3 and marker proteins further consisting of modifications and derivatives of marker proteins of Table 1, 2 or 3, so as to have at least 80% homology with marker proteins of Table 1, 2 or 3.

A method for diagnosing the predisposition in a human for diabetes, may comprise determining the increased expression in a biological sample from the human of at least one marker protein selected from the a biological sample from the human, said marker protein selected from the group consisting of proteins of Table 1, 2 and 3, establishing the decreased expression of at least one marker protein (a down-regulated marker protein) in a biological sample from the human, establishing the increased expression of at least one marker protein, or establishing combinations of increased and decreased expression of the marker proteins. Thus, the determination of whether a protein is up-regulated or down-regulated serves as useful indicators of diabetes susceptibility. The pattern of up and down regulation may also serve as an indicator. That is to say that the level of expression of more than one protein is established and the pattern of expression of a grouping of proteins is used as an indicator.

In a suitably embodiment, at least one marker protein is selected from the group consisting of one or more proteins present in a significantly lower or significantly higher amount on a polyacrylamide gel of proteins from said biological sample in relation to a control, one or more proteins present on a polyacrylamide gel of proteins from said biological sample and absent on polyacrylamide gel of proteins of a control, one or more proteins absent on a polyacrylamide gel of proteins from said biological sample and present on polyacrylamide gel of proteins of a control.

Similarly, with regards to a method of treating diabetes, a single protein may be targeted for therapy or a grouping of proteins may be targeted. The level of expression of these targeted proteins may be altered or the proteins themselves may be interfered with in order to alter their activity. Thus, an interesting embodiment of a method of treating diabetes in a human comprises altering the expressing of at least one marker protein of Table 1, 2 or 3.

The invention thus further relates to a method of treating diabetes in a human comprising administering at least one marker protein of Table 1, 2 or 3, a derivative, homologue or mimic thereof, a nucleotide sequence coding for a marker protein of Table 1, 2 or 3, an antibody for a protein of Table 1, 2 or 3, a nucleic acid fragment capable of binding to a marker protein (or its corresponding gene) of Table 1, 2 or 3, or a compound capable of binding to a marker protein (or its corresponding gene) of Table 1, 2 or 3 to said human.

A method of preventing or delaying the onset or of diabetes in a human according to the present invention may comprise administering a marker protein of Table 1, 2 or 3, a derivative, homologue or mimic thereof, a nucleotide sequence (such as DNA, cDNA, RNA, PNA homologues or mimics thereof) coding for a marker protein of Table 1, 2 or 3, an antibody for a protein of Table 1, 2 or 3, a nucleic acid fragment (such as DNA, cDNA, RNA, PNA, homologues or mimics thereof) capable of binding to a marker protein of Table 1, 2 or 3, or a compound capable of binding to a marker protein of Table 1, 2 or 3 (or its corresponding gene) to said human.

Thus a particularly interesting aspect of the present invention relates to a pharmaceutical composition which comprises a substance which is capable of regulating the expression of a nucleic acid fragment coding for at least a part of a protein of Table 1, 2 or 3, or at least one marker protein in Table 1, 2 or 3, an antibody for a protein of Table 1, 2 or 3, a nucleic acid fragment capable of binding to a marker protein of Table 1, 2 or 3, or a compound capable of binding to a marker protein of Table 1, 2 or 3 to said human.

The invention further relates to a method of determining the likelihood of an agent having a therapeutic effect in the treatment of diabetes comprising determining the level of expression of one or more proteins of Table 1, 2 or 3 before and after exposing a test model to said agent and comparing said levels.

In the testing of compounds, knowledge about the activity or target of an agent is useful for understanding the therapeutic activity of said agent and may assist in improving the desired therapy. The developments of the present investigators allows for a method of determining the effect of a compound in the treatment of diabetes comprising determining the level of expression of proteins of one or more proteins of Table 1, 2 or 3 and to a method of determining the level of effect or level of activity of a compound used in the treatment of diabetes comprising determining the level of expression of one or more proteins of Table 1, 2 or 3 before and after exposing a test model to said agent.

Thus, the invention further relates to a method for determining the physiological effect of a substance, the method comprising using a mammal which has been established to be an individual having a high likelihood of having diabetes or a genetic predisposition for having diabetes by use of a method according to the invention, the method comprising administering the substance to the individual and determining the effect of the substance. The present investigators anticipate that a method of determining the nature or cause of diabetes in a human having or susceptible to said disease comprising establishing the level of expression of a protein of Table 1, 2 or 3 in relation to a model serves for understanding the disease and potential therapies.

Each of the methods of the present invention relate to the use of a protein according to Table 1, 2 or 3 or having least 80% homology therewith and/or are post-translationally modified. Similarly, the newly identified proteins of Table 1, 2 or 3 further encompass proteins with at least 80% homology therewith, which are or are not post-translational modification products of these proteins.

The invention further relates to a nucleic acid fragment comprising a nucleotide sequence which codes for a peptide defined in Table 1, 2 or 3 as well as to a nucleic acid fragment which hybridizes with said nucleic acid fragment or a part thereof. The use of said nucleic acid fragment may serve to detecting the presence of a peptide of Table 1, 2 or 3.

The invention further relates to an antibody able to bind to a protein (or any part of its post-translational modification) defined in Table 1, 2 or 3. The antibody may be a polyclonal antibody or a monoclonal antibody. The use of an antibody may serve for detecting the presence of a peptide shown in Table 1, 2 or 3.

An interesting aspect of the present invention relates to a test kit for diagnosing diabetes or a genetic predisposition for diabetes in a mammal, comprising:

a) a binding mean which specifically binds to at least one marker protein shown in Table 1, 2 or 3 (or any part of its post-translational modification) or an antibody for a protein of Table 1, 2 or 3, a nucleic acid fragment capable of binding to a marker protein of Table 1, 2 or 3 (or any part of its post-translational modification), or a compound capable of binding to a marker protein of Table 1, 2 or 3 (or any part of its post-translational modification) to said human;

b) means for detecting binding, if any, or the level of binding, of the binding means to at least one of the marker proteins or at least one of the peptides or at least one of the nucleic acid fragments, and c) means for correlating whether binding, if any, or the level of binding, to said binding means is indicative of the individual mammal having a significantly higher likelihood of having diabetes or a genetic predisposition for having diabetes.

It should be noted that the detection of any combination of more than one of the markers would be expected to make the analysis an even more reliable indicator for the disease related to diabetes. Thus, a method for diagnosing or determining the predisposition of at least one disease related to diabetes comprising determining the presence, activity, concentration and/or level of expression of a combination of two markers would be preferred and three or more markers (e.g. at least 4, 5, 6 or 7 markers) would be strongly preferred. It is analogously suggested that treatment with more than one compound (e.g. at least 2, 3, 4, 5, 6 or 7 compounds) according to the invention (e.g. more than one compound chosen from the group consisting of: a polypeptide, a nucleic acid fragment or an antibody according to the invention), said compounds combined being able to affect the level of more than one marker protein, would make the treatment of the disease even more efficient.

Before the present human diabetes-mediating proteins and genes and assay methodology used in the assay are described, it is to be understood that this invention is not limited to particular assay methods, diabetes-mediating proteins and genes, test compounds described, as such methods, genes and preparations may, of course, vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, references to "diabetes-mediating protein" or "a diabetes-mediating protein" include mixtures of such diabetes-mediating proteins, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The term "diabetes" includes insulin-dependent diabetes mellitus (IDDM, juvenile diabetes or T1D) and type II diabetes (adult-onset diabetes, T2D). The term "diabetes-related diseases" includes such conditions as obesity, circulatory deficiencies, insulin-resistance, syndrome X, diabetic retinopathy, diabetic neuropathy, and the involvement of advanced glycation end products (AGE) in neuropathy and atherosclerosis.

The term "protein" includes proteins, polypeptides, and peptides which are chains of amino acids, including all post-translational modifications (e.g., processing and truncations, glycosylations or phosphorylations) which often play decisive roles in modulating protein function. The term also encompasses natural proteins as well as synthetic or recombinant proteins, polypeptides, and peptides. The term "diabetes-mediating protein" means a protein which is involved in the development of diabetes. A diabetes-mediating protein is a protein which exhibits an altered expression during the development of diabetes, that is, a protein which is up- or down-regulated, or whose expression is modulated up or down, during the development of diabetes, as compared to the expression of the same protein in the absence of the development of diabetes. In the present invention, a diabetes-mediating protein is identified as a human islet cell protein which exhibits altered expression as a result of exposure of a human islet cell to one or more cytokines, relative to the expression in a control cell which is not exposed to one or more cytokines.

The protein may be chemically or biochemically modified by being phosphorylated, methylated, sulphylated, glycosylated or by the addition of any form of lipid or fatty acid, ubiquitin or any other large side groups or by containing additional amino acids or any other forms of modification (of which there are over 200 known). These modifications occur at specific sites on the protein and a particular modification at one site can have different effects as the same modification at a different site on the same protein. They can be reversible in the cell where they are used for example to turn on and off enzymes and so the proteins can exist in a variety of forms-each with an associated activity level for each of the proteins functions. Furthermore the polypeptide may be cleaved e.g. by processing at its N- or C-termini to remove signal peptides or be spliced to remove an internal sequence. Examples of many of these can be found in the protein databases like EXPASY and there exist an ever growing range of tools to predict these modifications and their function. Since it is estimated that each protein in man is modified on average 10 times, it is expected that the majority of the proteins identified here are modified in some way or another. Their apparent isoelectric point and molecular weight has thus been given in tables 1, 2 and 3 so that they can be compared to the theoretical values to indicate what effects the modification has had on the protein.

The term "substantially pure," when referring to a polypeptide, means a polypeptide that is at least 60%, by weight, free from the proteins and naturally-occurring organic molecules with which it is naturally associated. A substantially pure diabetes-mediating protein is at least 75%, more preferably at least 90%, and most preferably at least 99%, by weight, diabetes-mediating protein. A substantially pure diabetes-mediating protein can be obtained, by extraction from a natural source; by expression of a recombinant nucleic acid encoding a diabetes-mediating protein, by recovery after electrophoresis of natural or recombinant cells or expression systems, or by chemically synthesizing the protein. Purity can be measured by any appropriate method, e.g., column chromatography, polyacrylamide gel electrophoresis, or HPLC analysis.

The term "protein" also encompasses derivatives, analogues and mimetics of the above mentioned polypeptides. Such a derivative, analogue and mimetic preferably have the same activity, e.g. the same kind of enzymatic activity, as the polypeptide which it is derived from. The derivative, analogue or mimetic can have a lower level activity, the same level or preferably, a higher level of activity than the parent polypeptide.

The term "at least one" (e.g. at least one compound or at least one marker protein) encompasses the integers 1, 2, 3, 4, 5, 6, 7, 8, 9, 10, 11, 12, 13, 14, 15, 16, 17, 18, 19 etc. It should be understood that a single marker protein can be used, but it can be advantageous to use more than one marker protein in methods of the invention. That is to say that the level of expression of more than one protein is established and the pattern of expression of a grouping of proteins is used as an indicator. Obviously the reliability of identification of diabetes increases as the number in the group increase.

A "peptide mimetic" is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide. The present invention encompasses peptidomimetic compositions which are analogs that mimic the activity of biologically active peptides according to the invention, i.e. the peptidomimetics can be used for treatment of diabetes related diseases. The peptidomimetic of this invention are preferably substantially similar in both three-dimensional shape and biological activity to the peptides or active sites of such as set forth above.

Alternatively, the mimetic can be an 'antimimetic'. In other words, a molecule that can fit into and block the active site of the protein, or bind to binding sites or sites of interaction with other biological molecules and so interfere with the function of the protein. Most current drugs are of this type. Such antimimetics that are capable of interacting with the polypeptides of the invention are encompassed by the present invention.

There are clear advantages for using a mimetic or an antimimetic of a given peptide rather than the peptide itself, because peptides commonly exhibit two undesirable properties: (1) poor bioavailability; and (2) short duration of action. Peptide mimetics or antimemetics offer an obvious route around these two major obstacles, since the molecules concerned are small enough to be both orally active and have a long duration of action. There are also considerable cost savings and improved patient compliance associated with peptide mimetics, since they can be administered orally compared with parenteral or transmucosal administration for peptides. Furthermore, peptide mimetics are much cheaper to produce than peptides. Finally, there are problems associated with stability, storage and immunoreactivity for peptides that are not experienced with peptide mimetics.

Thus peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide by NMR spectroscopy, crystallography and/or computer-aided molecular modelling. These techniques aid in the development of novel compositions of higher potency and/or greater bioavailability and/or greater stability than the original peptide [Dean (1994), BioEssays, 16: 683-687; Cohen and Shatzmiller (1993), J. Mol. Graph. 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference]. Once a potential peptidomimetic compound is identified, it may be synthesized and assayed using the diagnostic assay described herein or an appropriate disease suppressor assay [see, Finlay et al. (1983), Cell, 57: 1083-1093 and Fujiwara et al. (1993), Cancer Res., 53: 4129-4133, both incorporated herein by reference], to assess its activity.

Thus, through use of the methods described above, the present invention provides compounds exhibiting enhanced therapeutic activity in comparison to the polypeptides described above. The peptidomimetic compounds obtainable by the above methods, having the biological activity of the above named peptides and similar three dimensional structure, are encompassed by this invention. It will be readily apparent to one skilled in the art that a peptidomimetic can be generated from any of the modified peptides described previously or from a peptide bearing more than one of the modifications described previously. It will furthermore be apparent that the peptidomimetics of this invention can be further used for the development of even more potent non-peptidic compounds, in addition to their utility as therapeutic compounds.

The term "expression" is meant to include not only the physical expression of a protein, but also as a measure of the activity of an expressed protein. For example, a protein can be expressed as an inactive form, which is activated by phosphorylation. While the actual expression of the protein has not changed, its effective expression (activity) has been modified. On a gel, the change in activity may be measured as the change in expression of a modified form of the protein. By "altered protein" or "altered protein expression" is meant proteins whose expression is increased ("up regulated"), decreased ("down regulated"), inhibited (i.e., turned off), or induced (i.e., turned on) during the development of diabetes.

The term "diabetes-mediating gene or polynucleotide" means genetic material encoding a protein, peptide, or protein fragment which encodes an intact or fragment of a diabetes-mediating protein. The term includes any gene from any species which encodes a diabetes-mediating protein. A diabetes-mediating gene or polynucleotide may be naturally occurring or partially or wholly synthetic.

By the terms "nucleic acid fragment" "polynucleotide", "nucleic acid sequence" and the like are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length, e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least a part of the polypeptide is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives). It should be understood that these numbers can be freely combined to produce ranges.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences. The isolated and purified polynucleotide sequences of the invention also include polynucleotide sequences that hybridize under stringent conditions to the polynucleotide sequences specified herein.

The term "stringent conditions" means hybridization conditions that guarantee specificity between hybridizing polynucleotide sequences. One skilled in the art can select posthybridization washing conditions, including temperature and salt concentrations, which reduce the number of nonspecific hybridizations such that only highly complementary sequences are identified (Sambrook et al. (1989) in Molecular Cloning, 2d ed.; Cold Spring Harbor Laboratory Press, Cold Spring Harbor, N.Y., hereby specifically incorporated by reference). For instance, such conditions are hybridization under specified conditions, e.g. involving presoaking in 5×SSC and prehybridizing for 1 h at about 40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18 h at about 40° C. (Sambrook et al (1989) op cit.). The isolated and purified polynucleotide sequences of the invention also include sequences complementary to the polynucleotide encoding a diabetes-mediating protein (antisense sequences) and ribozymes. In the present application, the hybridization between polynucleotide sequences is preferably conducted under stringent conditions.

The term "sequence identity" (or "sequence homology") indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively truncation at the ends of the protein sequences. The sequence identity can be calculated as $(N_{ref} - N_{dif})100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8). A gap is counted as non-identity of the specific residue (s), i.e. the DNA sequence AGTGTC will have a sequence identity of 75% with the DNA sequence AGTCAGTC ($N_{dif}$=2 and $N_{ref}$=8). Sequence identity can alternatively be calculated by the BLAST program e.g. the BLASTP program (Pearson W. R and D. J. Lipman (1988) PNAS USA 85:2444-2448). In one aspect of the invention, alignment is performed with the sequence alignment method Clustal W with default parameters as described by Thompson J., et al Nucleic Acids Res 1994 22:4673-4680. Alternatively, the degree of homology between two nucleic acid sequences is determined by using GAP version 8 from the GCG package with standard penalties for DNA: GAP weight 5.00, length weight 0.300, Matrix described in Gribskov and Burgess, Nucl. Acids Res. 14(16); 6745-6763 (1986), and the degree of homology between two amino acid sequences is determined by using GAP version 8 from the GCG package (Genetics Computer Group, 575 Science Drive, Madison, Wis. 53711, USA) with standard penalties for proteins: GAP weight 3.00, length weight 0.100, Matrix described in Gribskov and Burgess, Nucl. Acids Res. 14 (16); 6745-6763 (1986).

A preferred minimum percentage of sequence homology is at least 70%, such as at least 80%, at least 85%, at least 90%, at least 91%, at least 92%, at least 93%, at least 94%, at least 95%, at least 96%, at least 97%, at least 98%, at least 99%, and at least 99.5%.

By the term "database" of proteins is meant a collection of proteins selected by possession of at least one common characteristic. The term "database" may be substituted by other terms designating a collection of proteins, including the term "library" or "array." The present invention provides a database of human islet cell proteins which exhibit, in one embodiment, the common characteristic of an altered expression when exposed to a specific combination of cytokines.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The invention also relates to the use of a polypeptide or nucleic acid of the invention for use as therapeutic vaccines as have been described in the literature exemplified by Lowry, D. B. et al 1999, Nature 400: 269-71.

A monoclonal or polyclonal antibody, which is specifically reacting with a polypeptide of the invention in an immuno assay, or a specific binding fragment of said antibody, is also a part of the invention. The antibodies can be produced by methods known to a person skilled in the art. The polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Kohler and Milstein, Nature, 256:495 (1975), or may be produced by recombinant DNA methods such as described in U.S. Pat. No. 4,816,567. The monoclonal antibodies may also be isolated from phage libraries generated using the techniques described by McCafferty et al, Nature, 348:552-554 (1990), for example. Further methods for producing antibodies are described in the literature, e.g. in U.S. Pat. No. 6,136,958.

In diagnostics, treatment or testing, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

The present invention is further directed to methods for using the compounds described above to therapeutically and/or prophylactically treat a patient for a diabetes related disease.

The methods of the present invention include the steps of: a) incorporating one or more of the compounds of the present invention in a suitable pharmaceutical carrier; and b) administering either a therapeutically effective amount or a prophylactically effective amount of the compound or compounds incorporated in the carrier to a patient.

The term "suitable pharmaceutical carrier" refers to any carrier known in the pharmaceutical arts for administration of compounds to a patient. Any suitable pharmaceutical carrier can be used according to the present invention, so long as compatibility problems do not arise.

Administration of an effective dosage to a patient can be accomplished by parenteral injection, such as intravenously, intrathecally, intramuscularly or intra-arterially. The compounds can also be administered orally or transdermally, or by any other means known to those skilled in the art, e.g. by means of an inhalator or a nasal spray. Oral administration is presently preferred.

As used herein, the term "therapeutically effective amount" refers to that amount of one or more of the compounds of the present invention required to therapeutically treating a patient. Such treatment is appropriate for subjects having a diagnosed diabetes related disease. Similarly, the term "prophylactically effective amount" refers to that amount of one or more of the compounds of the present invention needed to prophylactically treat a patient. Such treatment is appropriate for subjects who, for example, have not yet established any clinical symptoms of a diabetes related disease. It could be advantageous to start a prophylactic treatment as soon it is determined that the subject is in risk for developing a diabetes related disease, e.g. by means of a determination of a predisposition for diabetes by having an altered level of markers. It is known that certain markers for IDDM (e.g. $GAD_{65}$ and other autoantibodies) can be detected at least 8 years before the onset of the clinical symptoms.

As will be appreciated by a person skilled in the art, the dosage of compound given, the route of administration and the duration of therapy will be dependent not only the type of compound and its effectiveness in treating the disease but also upon the individual being treated, taking into consideration such factors as the body weight of the patient, other therapies being employed to treat the patient, and the condition, clinical response and tolerance of the patient. Dosage, administration, and duration of therapy can be determined by one skilled in the art upon evaluation of these and other relevant factors.

General Aspects of the Invention

Human Diabetes-Mediating Proteins and Polynucleotides

The invention provides human diabetes-mediating proteins, that is, proteins identified as involved in or effected during the development of diabetes. Diabetes-mediating proteins are characterized as proteins whose expression is altered during the development of diabetes relative to their expression in the absence of the development of diabetes. The present disclosure identifies diabetes-mediating proteins from a 2-dimensional gel database of human pancreatic islet cell proteins. Diabetes-mediating proteins include protective diabetes-mediating proteins and deleterious diabetes-mediating proteins. The diabetes-mediating proteins are identified by exposing human islet cells to cytokines which are known or accepted to be involved in the selective destruction of islet cells which precedes the eventual development of diabetes. The invention provides human diabetes-mediating proteins identified through the use of 2-dimensional gels to compare control and cytokine stimulated islets to identify which proteins respond, identifying the proteins which play a role in the cell response. Interlink analysis can be used to define functional groups of proteins and their regulation (e.g., by kinase phosphorylation or other post-translational modifications).

Protective Diabetes-mediating Proteins

The invention provides substantially purified protective diabetes-mediating proteins ("protective proteins") characterized as capable of protecting against development of diabetes in a subject at risk for the development of the disease or ameliorating or reducing the symptoms of diabetes in a subject suffering from diabetes. The protective protein of the invention may act directly to protect against diabetes, or may act indirectly by inducing or increasing the synthesis of a second protective protein or by reducing or inhibiting the synthesis of a deleterious protein. The invention further includes amino acid sequences having at least 80%, preferably at least 90%, more preferably at least 95% and most preferred at least 98% identity to the fully length amino acid sequence of a human diabetes-mediating protein. Percent homology or identity can be determined, for example, by comparing sequence information using the GAP computer program, version 6.0, available from the University of Wisconsin Genetics Computer Group (UWGCG). The GAP program utilizes the alignment method of Needleman and Wunsch (1970) J. Mol. Biol. 48:443, as revised by Smith and Waterman (1981) Adv. Appl. Math. 2:482. Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (1986) Nucl. Acids Res. 14:6745, as described by Schwartz and Dayhoff, eds. (1979) Atlas Of Protein Sequence And Structure, National Biomedical Research Foundation, pp. 353-358; (2) a penalty of 3.0 for each gap and an additional 0.10 penalty for each symbol in each gap; and (3) no penalty for end gaps.

The invention further includes polynucleotide sequences encoding the diabetes-mediating proteins of the invention, including DNA, cDNA, PNA and RNA sequences. It is also understood that all polynucleotides encoding all or a portion of a diabetes-mediating protein are also included herein, as long as they encode a polypeptide with the diabetes-mediating activity. Such polynucleotides include naturally occurring, synthetic, and intentionally manipulated polynucleotides. For example, such a polynucleotide may be subjected to site-directed mutagenesis. The polynucleotide sequences of the invention also include antisense sequences. Antisense sequences include sequences synthesized with modified oligonucleotides. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of the diabetes-mediating polypeptide is encoded by the nucleotide sequence is functionally unchanged.

Deleterious Diabetes-mediating Proteins

Deleterious diabetes-mediating proteins ("deleterious proteins") are characterized as enhancing the development of or increasing the risk of a subject developing diabetes.

Method for Identifying a Diabetes-mediating Protein

Two-dimensional gel electrophoresis (2-DGE) is a particularly effective tool for separating mixtures of proteins (e.g. Andersen et al. (1995) Diabetes 44:400-407; John N E et al., Diabetes. (2000); 49:1819-29. Christensen et al., Autoimmunity. (2000); 32:1-15 and Mose Larsen et al., Diabetes. (2001); 50: 1056-63). Cell protein extracts are put onto a gel, and the individual proteins are separated first by charge and then by size. The result is a characteristic picture of as many as 1,000 to 5,000 spots, each usually a single protein. Resolution is improved by increasing gel size, and by enhancing the sensitivity through the use of radiolabel methods, silver staining, and the reduction in thickness of the gels to 1.5 mm and less. A further significant improvement in resolution can be obtained by running first dimension gels covering narrow pH ranges (e.g. 1.5, 1 pH units or less). As described in the Examples below, single proteins recovered from 2D gels can be identified by mass spectrometry to obtain a trypsin cleavage pattern as well as the precise molecular weight of each peptide. These observed values are then used to search in DNA and protein databases to determine if matches exist to previously identified proteins. Identity can be determined from a known protein or deduced from high homology to a known protein. When 2D gel electrophoresis is used to separate and identify protein spots which exhibit an altered synthesis during development of diabetes, an identified protein spot is excised from the gel and digested with trypsin to produce peptides. The peptides are recovered from the gel and subjected to mass spectroscopy (matrix assisted laser desorption/ionization mass spectrometry)(MALDI) and the resulting MS-profiles are analyzed against the computerized MS-profiles of all sequences found in the public sequence databases, as well as against propriety sequence information. If any matches to previously cloned sequences are obtained, information about the corresponding gene and encoded protein is collected. When an identified diabetes-mediating protein does not match a previously cloned protein, the protein may be microsequenced to obtain partial amino acid sequence information by methods known to the art. Proteins (when available in sufficient quantities) may also be partially sequenced by for example nano-electrospray tandem mass spectrometry where particular peptides are fragmented in the gas phase and the molecular weights of the fragments used to derive part of the amino acid sequence. Once partial sequence information is available then it is also possible to search in the cDNA or EST (expressed sequence tag) databases in addition to those mentioned previously.

Based upon results obtained from database searches or amino acid sequencing, specific or degenerate primers are constructed and used to screen rat and human islets libraries or first-strand cDNA by PCR is used to clone partial sequences of the corresponding cDNA. The obtained sequences are then used to obtain full-length coding regions either by 5'-race PCR or by conventional hybridization screening techniques, followed by expression of the recombinant protein (Karlsen et al. (1991) Proc. Natl. Acad. Sci. USA 88:8337-8341; Karlsen et al. (1994) in: Insulin secretion and pancreatic beta-cell research, Flatt, P. R., ed., Smith-Gordon, USA; Chapter 64, pp. 1-9; Karlsen et al. (1995) Diabetes 44:757-758).

Diabetes-mediating proteins can be isolated in a variety of ways known to the art, including purification from biological material, expression from recombinant DNA (see above). Conventional method steps include extraction, precipitation, chromatography, affinity chromatography, and electrophoresis. For example, cells expressing a diabetes-mediating protein can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Diabetes-mediating proteins may alternatively be isolated by immunoprecipitation with the use of specific antibodies.

Use of Diabetes-Mediating Proteins for Screening of Compounds Capable of Effecting the Expression of a Diabetes-Mediating Protein Assay methods provided by the invention are useful for screen compounds capable of effecting the expression of a diabetes-mediating protein, and thus the development of diabetes in a mammal. One model for screening drugs capable of effecting the expression of one or more diabetes-mediating proteins is the administration of compounds suspected of having beneficial effects (including antisense oligonucleotides) to cells in culture. Useful cells are RIN, transfected, or islet cells. The effects of the test compound on protein expression may then be assayed by 2D gel electrophoresis. Another screening model is an in vivo method with the use of a mammal at risk for development of diabetes. Briefly, a mammal with an increased risk for diabetes (e.g., diabetes-prone BB rat or NOD mouse) is exposed to a test compound, and the effect of exposure to the test compound on the development of diabetes determined.

The development of diabetes may be monitored throughout the developmental period by determining the expression of one or more diabetes-mediating proteins and comparing by comparing the time of disease onset with expression and timing in the absence of disease development. Determining the expression of one or more diabetes-mediating proteins includes the diabetes-mediating protein itself, a post-translational modification product, and/or diabetes-mediating protein degradation product. In one embodiment, activation of a diabetes-mediating protein is determined by measuring the level of the diabetes-mediating protein expression in a test sample. A suitable test sample includes a body fluid, such as blood, urine, or cerebrospinal fluid, or fluid derived from it, such as plasma or serum. In a specific embodiment, the level of protein expression in a test sample is measured by Western blot analysis. The proteins present in a sample are fractionated by gel electrophoresis, transferred to a membrane, and probed with labeled antibodies specific for the protein(s). In another specific embodiment, the level of diabetes-mediating protein expression is measured by Northern blot analysis. Polyadenylated [poly(A)$^+$] mRNA is isolated from a test sample. The mRNA is fractionated by electrophoresis and transferred to a membrane. The membrane is probed with labeled cDNA. In another embodiment, protein expression is measured by quantitative PCR applied to expressed mRNA.

In yet another aspect, the invention provides for methods for identifying compounds capable of suppressing or reducing the expression of an endogenous deleterious protein, as well as methods for preventing and/or treating diabetes by administering a therapeutically effective among of a compound capable of suppressing or reducing the expression of an endogenous deleterious protein.

The diabetes-mediating proteins of the invention are also useful to screen reagents that modulate diabetes-mediating protein activity. Accordingly, in one aspect, the invention features methods for identifying a reagent which modulates diabetes-mediating protein activity, by incubating a cell expressing a diabetes mediating protein with the test reagent and measuring the effect of the test reagent on diabetes-mediating protein synthesis, phosphorylation, function, or activity. When activation of a diabetes-mediating protein is via phosphorylation, the test reagent is incubated with the diabetes-mediating protein and with either gamma-[$^{32}$P] or [$^{33}$P]-labeled-ATP (or other mono-nucleotides), or [$^{32}$P] or [$^{33}$P]-pyrophosphate (phosphoric acid) or [$^{35}$S]-methionine, and the rate of phosphorylation determined. In another embodiment, the test reagent is incubated with a cell transfected with an diabetes-mediating protein polynucleotide expression vector, and the effect of the test reagent on diabetes-mediating protein transcription is measured by Northern blot analysis. In a further embodiment, the effect of the test reagent on diabetes-mediating protein synthesis is measured by Western blot analysis using an antibody to the diabetes-mediating protein in still another embodiment, the effect of a reagent on diabetes-mediating protein activity is measured by incubating diabetes-mediating protein with the test reagent, [$^{32}$P]-ATP (or other radiochemicals mentioned above), and a substrate in the diabetes-mediating protein pathway. All experiments would be compared against a normal labelling of cells with [$^{35}$S]-methionine to determine modulation of protein expression. The rate of substrate phosphorylation is determined by methods known in the art.

The term modulation of diabetes-mediating protein activity includes agonists and antagonists. The invention is particularly useful for screening reagents that inhibit deleterious protein activity. Such reagents are useful for the treatment or prevention of diabetes.

Therapeutic Applications

The invention provides methods for preventing and/or treating diabetes in a human by administering a therapeutically effective amount of a protective diabetes-mediating protein. Preferably the mammal is a human subject at risk for diabetes.

Drug Screening Using Identified Diabetes-mediating Proteins and Related Diabetes Therapeutic Agents In a drug-screening assay of the invention, identified protective or deleterious diabetes-mediating proteins are used to identify test compounds capable of effecting their expression. Test compounds so identified are candidate therapeutic agents for preventing, ameliorating, or delaying the onset of diabetes in a subject at risk.

A test therapeutic compound which effects the expression of a diabetes-mediating proteins can be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds.

A therapeutic compound is identified in the drug screening assay of the invention through its ability to induce or enhance the expression of a protective protein, such that disease onset is prevented or delayed in a subject at risk for the development of diabetes. A candidate therapeutic compound is also identified by its ability to prevent or decrease the expression of a deleterious protein, such that disease onset is prevented or delayed in a subject at risk for the development of diabetes. A therapeutic nucleic acid as a therapeutic compound can have, but is not limited to, at least one of the following therapeutic effects on a target cell: inhibiting transcription of a deleterious protein DNA sequence; inhibiting translation of a deleterious protein RNA sequence; inhibiting reverse transcription of an RNA or DNA sequence corresponding to a deleterious protein; inhibiting a post-translational modification of a protein; inducing transcription of a DNA sequence corresponding to a protective protein; inducing translation of an RNA sequence corresponding to a protective protein; inducing reverse transcription of an RNA or DNA sequence corresponding to a protective protein; translation of the nucleic acid as a protein or enzyme; and incorporating the nucleic acid into a chromosome of a target cell for constitutive or transient expression of the therapeutic nucleic acid. Therapeutic effects of therapeutic nucleic acids can include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or under-expression of an RNA such as an hnRNA, an mRNA, a tRNA, or an rRNA; encoding a drug or prodrug, or an enzyme that generates a compound as a drug or prodrug in pathological or normal cells expressing the diabetes-mediating protein or peptide; and any other known therapeutic effects. Also included in the invention is gene therapy by providing a polynucleotide encoding a protective diabetes-mediating protein. The invention further includes a method for preventing diabetes by administering an effective amount of a polynucleotide which inhibits the in vivo expression of a deleterious diabetes-mediating protein.

In the therapeutic method of the invention, a therapeutic compound is administered to a human patient chronically or acutely. Optionally, a protective protein is administered chronically in combination with an effective amount of a compound that acts on a different pathway than the therapeutic compound. The therapeutic method of the invention can be combined with other treatments for diabetes or with methods for the management of diabetes. Therapeutic formulations are described in PCT/IB97/01627, which text is specifically incorporated herein by reference for the description of therapeutic formulations and the administration of therapeutic compounds known to the art, including conventional and gene therapeutic techniques.

Identification and Characterization of Human Diabetes-Mediating Proteins

As described in the Example below, human islet of Langerhans isolated from the pancreas of organ donors were cultured under standard culture conditions in RPMI 1640 medium in the presence of recombinant cytokines as follows:

A=culture medium alone;
B=culture medium+150 pg/ml interleukin-1β (IL-1β) (equivalent to 60 U/ml);
C=culture medium+1500 pg/ml IL-1β;
D=culture medium+1000 U/ml-IFN-γ+5000 U/ml tumour necrosis factor-α (TNFα);
E=150 pg/ml IL-1β+1000 U/ml IFNγ+5000 U/ml TNFα.

After incubation for 20 hr under standard cell culture conditions, cells were labelled in the presence of [$^{35}$S]- methionine for 4 hours. Proteins were isolated from both cells and culture media. Proteins obtained from culture media represent proteins secreted as a result of exposure to none, one or more cytokines. Protein samples were analyzed by 2-D gel electrophoresis and mass spectroscopy.

For analytical gels, used for the identification of proteins of altered expression level, 6 individual experiments were performed with 150 islets in each experiment. This allowed the construction of a composite Image of each culture condition. Thus, comparison and statistical evaluation between the control condition (A) and any of the other conditions of cytokine exposure (B-E) by this means allowed identification of a set of proteins in the islets as well as secreted to the medium, that were significantly up- or down-regulated compared to the control situation. In order to MS identify the protein behind the spots identified as up-or downregulated in the analytical gel analysis described above, quantitative/preparative gels with 100,000 islets per conditions were made (to get sufficient amount of protein in each spot to allow MS identification). Thus, two sets of 100.000 islets were cultured in the absence of cytokines (A) or in the presence of the 3 cytokines (E), to increase the chance to have all protein spots of interest available for the MS identification.

Experimental

The following examples are put forth so as to provide those of ordinary skill in the art with a complete disclosure and description of how to make and use the proteins, genes and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Materials and Methods

Reagents

Ketamin was purchased from Park-Davis (Barcelona, Spain), xylazin from Bayer (Leverkusen, Germany), and Temgesic® from Reckitt and Colemann (Hull, UK). RPMI 1640, Hanks' balanced salt solution (HBSS), and DMEM were purchased from Gibco, Paisley, Scotland. RPMI 1640 contained 11 mmol D-glucose, and was supplemented with 20 mM HEPES buffer, 100,000 IU/l penicillin and 100 mg/l streptomycin. Authentic recombinant human IL-1β was provided by Novo Nordisk Ltd. (Bagsvaerd, Denmark) having a specific activity of 400 U/ng.

Other reagents used: 2-mercaptoethanol, bovine serum albumin (BSA), Tris-HCl, Tris base, glycine, (Sigma, St. Louis, USA); trichloracetic acid (TCA), phosphoric acid, NaOH, glycerol, n-butanol, bromophenol blue, sodium nitroprusside (SNP), $H_3PO_4$ and $NaNO_2$ (Merck, Darmstadt, Germany); filters (HAWP 0.25 mm pore size) (Millipore, Boston, USA); RNAse A, DNAse I (Worthington, Freehold, N.J., USA); [$^{35}$S]-methionine (SJ 204, specific activity: >1.000 Ci/mmol, containing 0.1% 2-mercaptoethanol), Amplify® (Amersham International, Amersham, UK); urea (ultra pure) (Schwarz/Mann, Cambridge, Mass., USA); acrylamide, bisacrylamide, TEMED, ammonium persulphate (BioRad, Richmond, Calif., USA); ampholytes: pH 5-7, pH 3.5-10, pH 7-9, pH 8-9.5 (Pharmacia, Uppsala, Sweden); Nonidet P-40

(BDH, Poole, UK); ampholytes: pH 5-7 and sodium dodecyl sulphate (Serva, Heidelberg, Germany); agarose (Litex, Copenhagen, Denmark); ethanol (absolute 96%) (Danish Distillers, Aalborg, Denmark); methanol (Prolabo, Brione Le Blanc, France); acetic acid (technical quality, 99% glacial) (Ble & Berntsen, Århus, Denmark) and X-ray film (Curix RP-2) (AGFA).

Human Samples

Human islets were isolated (Andersen et al. (1995) Diabetes 44:400-407; John N E et al., Diabetes. (2000); 49:1819-29. Christensen et al., Autoimmunity. (2000); 32:1-15 and Mose Larsen et al., Diabetes. (2001); 50: 1056-63) and provided by the Diabetes Research Inst., Division of Cellular Transplantation, Miami, Fla., USA. After a few days of culture, the islets were exposed to the experimental conditions detailed above. At the end of the experiments the washed islets and culture/labelling media were either directly (for preparative gels) or following lysis in sample buffer (for analytical gels) immediately stored at −80° C. prior to 2D-gel analysis.

Cytokine Challenge

The prepared human islet cells were cultured in five different experimental conditions: Group A was cultured in culture medium alone; Group B in culture medium+150 pg/ml IL-1β (equivalent to 60 U/ml); Group C in culture medium+1500 pg/ml IL-1β; Group D in culture medium +1000 U/ml IFNγ+ 5000 U/ml TNFα; and Group D in 150 pg/ml IL-1β+1000 U/ml IFNγ+5000 U/ml TNFα. The cells were incubated for 20 hours at 37° C. under standard culture conditions, followed by 4 hr incubation with [$^{35}$S]-methionine. Cells were collected for 2-D gel electrophoresis and mass spectrophotometric analysis. Labelled media was collected from each experimental group for analysis of secreted proteins.

Sample Preparation

Whereas the 150 islets/condition used for the analytical part were directly lysed in lysis buffer, the larger number of islets (100,000/condition) cultured under conditions A and E to be used for the preparative gels and MS identification as described above, were crushed in a mortar and resuspended in 100 ml DNAse I/RNAse A solution and lysed by freeze/thawing twice. After the second thawing, the samples were left on ice for 30 min for the digestion of nucleic acids and then freeze dried overnight. The samples were dissolved by shaking in 120 ml lysis buffer (8.5 M urea, 2% Nonidet P-40, 5% 2-mercaptoethanol and 2% ampholytes, pH range 7-9) for a minimum of 4 h before 2D-gel separation.

Determination of [$^{35}$S]-methionine Incorporation

The amount of [$^{35}$S]-methionine incorporation was quantitated by adding 10 mg BSA (0.2 mg/ml $H_2O$) as a protein carrier to 5 ml of a 1:10 dilution of each sample in duplicate, followed by 0.5 ml of 10% TCA. This was left to precipitate for 30 min at 4° C. before being filtered through 0.25 mm HAWP filters. The filters were dried and placed into scintillation liquid for counting.

2-D Gel Electrophoresis

The procedure has been described earlier (O'Farrell et al. (1977) Cell 12:1133-1142). Briefly, first dimension gels contained 4% acrylamide, 0.25% bisacrylamide and ampholytes. Equal numbers of counts ($10^6$ cpm) of each sample were applied to the gels. In case of lower amounts of radioactivity it was necessary to regulate the exposure time of the gel so that comparable total optical densities were obtained. The samples were analyzed on both isoelectric focusing (IEF; pH 3.5-7) and non-equilibrium pH-gradient electrophoresis (NEPHGE; pH 6.5-10.5) gels. Second dimension gels contained 12.5% acrylamide and 0.063% bisacrylamide and were run over-night. After electrophoresis, the gels were fixed and treated for fluorography with Amplify® before being dried. The gels were placed in contact with X-ray films and exposed at −70° C. for 3 to 40 days. Each gel was exposed for at least 3 time periods to compensate for the lack of dynamic range of X-ray films. Some gels were dried immediately and the gel exposed to a phosphorimaging plate to capture the image. After exposure for from 3 to 15 days (1 exposure per gel because the phosphorimager's dynamic range is in excess of $10^6$), the plates were read in an AGFA ADC 70 and the images exported for analysis as 16 bit files.

Determination of MW and pI

Molecular weights of the proteins were determined by interpolation using values from known proteins. Landmark proteins were identified on gels by one or several of the following techniques: immunoblotting, immunoprecipitation, mass spectrometry, microsequencing or peptide mapping.

Computer Analysis of Fluorographs

Computer analysis was performed using the BioImage® program (version 6.1) on a Sunsparc workstation. First, the fluorographs or autoradiographs were scanned and spots identified and quantitated by the BioImage® program. Next, anchor points were placed on the gel (same spot in each gel was assigned the same anchorpoint), and the computer was asked to match the gels. After computer matching, manual editing was performed to ensure correct spot boundary identification, correct matching of computer found spots and quantitation of spots not found initially by the computer program. Finally, data were extracted for calculations in the Excel® spreadsheet (Microsoft). To avoid the presence of duplicate spots in the IEF and NEPHGE subgroups, overlapping spots in either the basic part of IEF gels or in the acidic part of NEPHGE gels were omitted from analysis.

Statistical Analysis

Student's t test was applied and P<0.01 was chosen as level of significance.

EXAMPLE 2

Characterization of Diabetes-Mediated Proteins

Mass Spectroscopy

In situ digestion is performed on at least one gel plug including at least one protein spot in at least one gel according to the present invention. Gels are prepared by a modification of the method of Rosenfeld et al. (1992) Anal. Biochem. 203:173-179, as described in Fey et al. (1997) Electrophoresis 18:1-12, both of which references are herein specifically incorporated by reference. Briefly, gels are quickly stained and destained. The protein of interest is obtained by cutting a gel band containing the protein with a scalpel and storing in eppendorf tubes with UHQ water at −20° C. The protein is digested by washing the gel plug for at least 1 hour in 40% acetonitrile/60% digestion buffer until the coomassie stain is removed.

This wash removes coomassie stain, gel buffers, SDS and salts. If necessary the wash can be repeated. The gel plug is then dried in a vacuum centrifuge for 20-30 min. until the plug shrinks and becomes white on the surface. Drying time depends on the size and thickness of the gel plug. Trypsin (or the enzyme being used is dissolved in digestion buffer and 5 mls added to the gel plug (depending on the amount of the protein in the gel to be analyzed (0.1 mg)). Additional digestion buffer is added until the gel plug is almost covered by buffer in the bottom of the tube, approximately 10 ml. The gel plug is then incubated at 37° C. for 6 hours or overnight, then incubated with 70-100 ml 60% acetonitrile/40% water for 2-6 hours to extract the peptides. The extraction may be repeated to increase recovery. The extract is then lyophilized and dissolved in 30% acetonitrile/2%TFA before analyzing by MALDI-MS.

EXAMPLE 3

Quantitative Gel Analysis

Analysis of the two-dimensional gels described above resulted in identification of a database of human diabetes-mediating proteins listed in Tables 1-8. These proteins have been identified by treating human islets with either 1500 pg/ml IL-1β or with a mixture of cytokines (150 pg/ml IL-1β (beta interleukin), 1000 U/ml IFNγ (gamma interferon), and 5000 U/ml TNFα (alpha tumour necrosis factor).

Table 1 lists all cellular proteins identified as exhibiting a statistically significant altered expression when [$^{35}$S]-methionine labelled human islets are treated with cytokines and the proteins analysed on IEF gels. In each of the tables 1, 2, and 3 IL-1β 1500 refers to the stimulation by 1500 pg/ml IL-1β. 'Cytokine mix' refers to the stimulation induced by 150 pg/ml IL-1β, 1000 U/ml IFNγ, and 5000 U/ml TNFα. An arrow pointing up indicates that the protein is expressed in higher amounts in the treated cells; and a downward pointing arrow, the reverse.

Table 2 lists all cellular proteins identified as exhibiting a statistically significant altered expression when [$^{35}$S]-methionine labelled human islets are treated with cytokines and the proteins analysed on NEPHGE gels.

Table 3 lists all secreted proteins identified as exhibiting a statistically significant altered expression or secretion when [$^{35}$S]-methionine labelled human islets are treated with cytokines and the proteins analysed on IEF gels.

Table 4 lists human islet cell proteins identified as exhibiting an altered expression upon cytokine challenge when analysed on IEF gels (cf. Table 1) and provides the mass spectroscopy molecular weight values obtained for the protein fragments. These proteins have been identified by reference to proteins from other species recorded in publicly available databases (including amino acid and nucleotide sequences).

Table 5 lists human islet cell proteins identified as exhibiting an altered expression upon cytokine challenge when analyzed on NEPHGE gels (cf. Table 2) and provides the mass spectroscopy molecular weight values obtained for the protein fragments. The proteins have been identified by reference to proteins from other species recorded in publicly available databases (including amino acid and nucleotide sequences).

Table 6 lists novel human islet cell proteins identified from IEF gels (cf. Table 1) which did not correspond to any known protein and provides the mass spectroscopy molecular weight values obtained for the protein fragments.

Table 7 lists novel human islet cell proteins identified from NEPHGE gels (cf. Table 2) which did not correspond to any known protein and provides the mass spectroscopy molecular weight values obtained for the protein fragments.

Table 8 lists proteins secreted by human islet cells identified from IEF gels (cf. Table 3) which did not correspond to any known protein and provides the mass spectroscopy molecular weight values obtained for the protein fragments.

FIG. 1 shows a two dimensional gel image of human islets that have been labelled with [$^{35}$S]-methionine and the proteins separated according to the procedures described herein. Proteins mentioned in the text or tables are marked in for reference. Approximate molecular weight scale is given on the right. The image is presented with the acidic side to the right and covering the nominal pH range of 4 to 7.

FIG. 2 shows a two dimensional gel image of human islets that have been labelled with [$^{35}$S]-methionine and the proteins separated according to the procedures described herein. Proteins mentioned in the text or tables are marked in for reference as is an indicative molecular weight scale. The image is presented with the acidic side to the right and covering the nominal pH range of 6.5 to 10.5.

FIG. 3 shows a two dimensional gel image of human proteins secreted by islets that have been labelled with [$^{35}$S]-methionine and the proteins separated according to the procedures described herein. Proteins mentioned in the text or tables are marked in for reference as is an indicative molecular weight scale. The image is presented with the acidic side to the right and covering the nominal pH range of 4 to 7.

TABLE 1

HUMAN ISLET CELL PROTEINS CHARACTERISED BY MS. IDENTIFIED, IDENTIFIED BY RELATION TO ANOTHER SPECIES AND UNIDENTIFIED PROTEINS.

| Spot # | Gene Name | Identifier | Il1β 1500 | Cyt. Mix | Name Protein | Obs. pI | Mol. Wt |
|---|---|---|---|---|---|---|---|
| 8 | | | | ↓ | Novel spectrum see table 6 | 4.79 | 249,415 |
| 191 | HS74 | P34932 | | ↓ | Heat shock 70 kD protein 4 (HSP70RY) HSPA4. | 4.95 | 127,654 |
| 267 | EZRI | P15311 | | ↓ | Ezrin (P81) (Cytovillin) (Villin-2) VIL2 | 6.34 | 69,286 |
| 297 | | | | ↓ | Novel unidentified protein | 5.90 | 76,695 |
| 370 | | | | ↓ | Novel spectrum see table 6 | 5.15 | 88,075 |
| 473 | | | ↓ | ↓ | Novel spectrum see table 6 | 6.31 | 69,863 |
| 504 | HS7C | P11142 | | ↑ | Heat shock cognate 71 kD protein HSPA8 OR HSC70 OR HSP73 | 5.96 | 62,425 |
| 524 | | | | ↑ | Novel spectrum see table 6 | 5.78 | 63,041 |
| 535 | | | | ↑ | Novel spectrum see table 6 | 5.60 | 70,495 |
| 551 | | | | ↑ | Novel spectrum see table 6 | 5.53 | 70,096 |
| 554 | | | | ↓ | Novel unidentified protein | 5.40 | 66,003 |
| 651 | | | ↓ | | Novel spectrum see table 6 | 4.67 | 78,015 |
| 656 | | | | ↓ | Novel spectrum see table 6 | 4.65 | 69,924 |
| 677 | | | ↑ | ↑ | Novel unidentified protein | 6.84 | 68,176 |

TABLE 1-continued

HUMAN ISLET CELL PROTEINS CHARACTERISED BY MS. IDENTIFIED, IDENTIFIED BY RELATION TO ANOTHER SPECIES AND UNIDENTIFIED PROTEINS.

| Spot # | Gene Name | Identifier | Il1β 1500 | Cyt. Mix | Name Protein | Obs. pI | Mol. Wt |
|---|---|---|---|---|---|---|---|
| 699 | DHAX | P49419 | ↓ | ↓ | Inosine-5'-monophosphate dehydrogenase 2 (EC 1.1.1.205) (IMP dehydrogenase 2) (IMPDH-II) (IMPD 2) IMPDH2 OR IMPD2. | 6.46 | 61,913 |
| 699 | IMD2 | P12268 | ↓ | ↓ | Inosine-5'-monophosphate dehydrogenase 2 (EC 1.1.1.205) (IMP dehydrogenase 2) (IMPDH-II) (IMPD 2) IMPD2 OR IMPD2. | 6.46 | 61,913 |
| 699 | DHAC | P00352 | ↓ | ↓ | Aldehyde dehydrogenase, cytosolic (EC 1.2.1.3) (class 1) (ALHDII) ALDH-E1 ALDH1 or ALDC | 6.46 | 61,913 |
| 724 | AMPL | P00727 | | ↑ | BOVINE Cytosol aminopeptidase (EC 3.4.11.1) (Leucine amino-peptidase) (LAP) | 6.32 | 57,846 |
| | | | | ↑ | See table 4 (Leucyl aminopeptidase) (proline aminopeptidase) (EC 3.4.11.5) (prolyl aminopeptidase) | | |
| 724 | DHAC | P00352 | | ↑ | Aldehyde dehydrogenase, cyto-solic (EC 1.2.1.3) (class 1) (ALHDII) (ALDH-E1) | 6.32 | 57,846 |
| 725 | DHAC | P00352 | ↓ | ↓ | Aldehyde dehydrogenase, cyto-solic (EC 1.2.1.3) (class 1) (ALHDII) (ALDH-E1) | 6.30 | 56,853 |
| 760 | SYW | P23381 | ↑ | ↑ | Tryptophanyl-tRNA synthetase (EC 6.1.1.2) (Tryptophan-tRNA ligase) | 5.78 | 52,099 |
| 763 | | | ↑ | ↑ | Novel unidentified protein | 5.71 | 52,172 |
| 812 | P60 | P10809 | ↓ | ↓ | Mitochondrial matrix protein P1 (P60 lymphocyte protein) 60 kD Chaperonin (heat shock protein 60) HSP-60 (protein CPN60) (GROEL) (HUCHA60) | 5.15 | 55,253 |
| 826 | YPH | P19971 | | ↑ | Thymidine phosphorylase (EC 2.4.2.4) (TDRPase) (platelet-derived endothelial cell growth factor) (PD-ECGF) (gliostatin) ECGF1 | 5.14 | 50,432 |
| 855 | TBA1 | P04687 | | ↑ | Tubulin alpha-1 chain TUBA1 | 4.93 | 57,204 |
| 855 | TBB1 | P07437 | | ↑ | Tubulin beta-1 chain | 4.93 | 57,204 |
| 855 | HSU5 2513 | Q99634 | | ↑ | RIG-G | 4.93 | 57,204 |
| 864 | TBB1 | P07437 | ↓ | ↓ | Tubulin beta-1 chain.TUBB1 | 4.76 | 54,251 |
| 864 | TBB2 | P05217 | ↓ | ↓ | Tubulin beta-2 chain.TUBB2 | 4.76 | 54,251 |
| 864 | PDI | P07237 | ↓ | ↓ | Protein disulfide isomerase (PDI) (EC 5.3.4.1) Prolyl 4-hydroxylase beta subunit (EC 1.14.11.2) Cellular thyroid hormone binding protein (P55) | 4.76 | 54,251 |
| 864 | CBPH | P16870 | ↓ | ↓ | Carboxypeptidase H (EC 3.4.17.10) (CPH) (Carboxypeptidase E) (CPE) (Enkephalin convertase) (prohormone processing carboxypeptidase) | 4.76 | 54,251 |
| 909 | | | ↓ | ↓ | Novel spectrum see table 6 | 4.41 | 64,739 |
| 963 | IDHC | P41562 | | ↑ | RAT Isocitrate dehydrogenase (NADP) cytoplasmic (EC 1.1.1.42) (Oxalo-succinate de-carboxylase) (IDH)(NADP+-spe-cific ICDH) (IDP) IDH1 See table 4 | 6.40 | 47,310 |
| 971 | GATM | P50440 | | ↓ | Glycine amidinotransferase (EC 2.1.4.1) (L-arginine: glycine amidinotransferase) (transamidinase) AGAT | 6.30 | 49,264 |
| 977 | NUCM | P17694 | | ↓ | BOVINE NADH-Ubiquinone oxido-reductase 49 kD subunit (EC 1.6.5.3)(EC 1.6.99.3) (Complex I 49 kD)(CI-49 kD) NDUFS2 See table 4 | 6.36 | 45,388 |
| 989 | GATM | P50440 | | ↓ | Glycine amidinotransferase (EC 2.1.4.1) (L-arginine: glycine amidinotransferase) (transamidinase) AGAT | 6.27 | 47,318 |
| 1001 | SYW | P23381 | | ↑ | Tryptophanyl-tRNA synthetase (EC 6.1.1.2) (Tryptophan-tRNA ligase) | 5.93 | 45,147 |
| 1012 | SYW | P23381 | ↓ | ↑ | Tryptophanyl-tRNA synthetase (EC 6.1.1.2) (Tryptophan-tRNA ligase) | 5.82 | 45,316 |

TABLE 1-continued

HUMAN ISLET CELL PROTEINS CHARACTERISED BY MS. IDENTIFIED, IDENTIFIED BY RELATION TO ANOTHER SPECIES AND UNIDENTIFIED PROTEINS.

| Spot # | Gene Name | Identifier | Il1β 1500 | Cyt. Mix | Name Protein | Obs. pI | Mol. Wt |
|---|---|---|---|---|---|---|---|
| 1012 | PRS7 | P35998 | ↓ | ↑ | 26S Protease Regulatory Subunit 7 (MSS1 PROTEIN). | 5.82 | 45,316 |
| 1013 | | | | ↑ | Novel spectrum see table 6 | 5.79 | 44,636 |
| 1022 | DHAG | P49189 | ↑ | ↑ | Aldehyde dehydrogenase, E3 isozyme (EC 1.2.1.3) (Gamma-aminobutyraldehyde dehydrogenase) (EC 1.2.1.19) (R-aminobutyraldehyde dehydrogenase). | 5.71 | 44,824 |
| 1159 | RINI | P13489 | | ↑ | Placental ribonuclease inhibitor (Ribonuclease/an-giogenin inhibitor)(RAI)(RI) | 4.50 | 48,395 |
| 1170 | GR75 | P38646 | ↑ | ↑ | Mortalin, Mitochondrial stress-70 protein (75 KD Glu-cose Regulated Protein) GRP 75 | 6.74 | 34,598 |
| 1176 | | | ↑ | | Novel unidentified protein | 6.50 | 42,222 |
| 1186 | | | ↑ | | Novel spectrum see table 6 | 6.46 | 36,234 |
| 1210 | NED5 | Q15019 | | ↓ | NEDD5 protein homolog (KIAA0158) NEDD5 or DIFF6) | 6.14 | 40,411 |
| 1221 | 1A32 | P10314 | | ↑ | HLA class I histocompatibility antigen, A-32(AW-19) alpha chain HLA-A OR HLAA | 5.91 | 39,707 |
| 1241 | ANX4 | P09525 | | ↑ | Annexin IV (Lipocortin IV) (Endonexin I) (Chromobindin 4) (Protein II) (P32.5) (Placen-tal anticoagulant protein II) (PAP-II) (PP4-X) (35-beta Cal-cimedin) (Carbohydrate-binding protein P33/P41) | 5.64 | 38,609 |
| 1241 | DCUP | P06132 | | ↑ | Uroporphyrinogen decarboxylase (EC 4.1.1.37) (URO-D) UROD | 5.64 | 38,609 |
| 1349 | ANX2 | P07355 | | ↓ | Annexin II (Lipocortin II) (Calpactin I heavy chain) (Chromobindin 8) (P36) (prtein I) (Placental anticoagulant protein IV) (PAP-IV) | 6.70 | 32,626 |
| 1353 | | | ↑ | | Novel spectrum see table 6 | 6.68 | 32,210 |
| 1368 | ANX4 | P09525 | ↓ | ↓ | Annexin IV (Lipocortin IV) (Endonexin I) (Chromobindin 4) (Protein II) (P32.5)(Placental anticoagulant protein II) (PAP-II) (PP4-X) (35-beta Calcimedin) (Carbohydrate-binding pro-tein P33/P41) | 6.36 | 30,916 |
| 1376 | G3P2 | P04406 | | ↑ | Glyceraldehyde 3-phosphate dehydrogenase, Liver EC 1.2.1.12 | 6.19 | 34,534 |
| 1376 | ANX2 | P07355 | | ↑ | Annexin II (Lipocortin II) (Calpactin I heavy chain) (Chromobindin 8) (P36) (protein I) (Placental anticoagul-ant protein IV) (PAP-IV) ANX2 | 6.19 | 34,534 |
| 1400 | | | | ↓ | Novel spectrum see table 6 | 5.77 | 33,725 |
| 1411 | ANX4 | P09525 | | ↑ | Annexin IV (Lipocortin IV) (Endonexin I) (Chromobindin 4) (Protein II) (P32.5) (Placen-tal anticoagulant protein II) (PAP-II) (PP4-X) (35-beta cal-cimedin) (Carbohydrate-binding protein P33/P41) | 5.49 | 31,904 |
| 1421 | ANX2 | P07355 | | ↑ | Annexin II (Lipocortin II) (Calpactin I heavy chain) (Chromobindin 8) (P36) (protein I) (Placental anticoagulant protein IV) (PAP-IV) | 5.43 | 33,800 |
| 1421 | IPYR | P37980 | | ↑ | BOVINE Inorganic pyrophosphatase (EC 3.6.1.1) (Pyrophosphate phospho-hydrolase) (PPASE) PP See table 4 | 5.43 | 33,800 |
| 1426 | ANX2 | P07355 | | ↑ | Annexin II (Lipocortin II) (Calpactin I heavy chain) (Chromobindin 8) (P36) (protein I) (Placental anticoagulant protein IV) (PAP-IV) | 5.28 | 33,836 |
| 1477 | | | | ↑ | Novel spectrum see table 6 | 4.48 | 35,393 |
| 1531 | IGUP | Q06323 | ↑ | ↑ | Interferon gamma up-regulated I-5111 protein (IGUP I-5111) | 5.68 | 28,980 |

TABLE 1-continued

HUMAN ISLET CELL PROTEINS CHARACTERISED BY MS. IDENTIFIED, IDENTIFIED BY RELATION TO ANOTHER SPECIES AND UNIDENTIFIED PROTEINS.

| Spot # | Gene Name | Identifier | Il1β 1500 | Cyt. Mix | Name Protein | Obs. pI | Mol. Wt |
|---|---|---|---|---|---|---|---|
| 1545 | CAPB | P47756 | ↑ | | F-Actin capping protein beta subunit (CAPZ) CAPZB. | 5.36 | 28,940 |
| 1545 | CATD | P07339 | ↑ | | Cathepsin D (EC 3.4.23.5) CTSD | 5.36 | 28,940 |
| 1545 | PRC2 | P25786 | ↑ | | Proteasome component C2 (EC 3.4.99.46) (Macropain subunit C2) (Proteasome NU chain) (multicatalytic endopeptidase complex subunit C2) (30 kD prosomal protein) (PROS-30) PSMA1 or PSC2 or PROS30 | 5.36 | 28,940 |
| 1549 | | | | ↑ | Novel spectrum see table 6 | 5.40 | 28,949 |
| 1609 | SODM | P04179 | ↑ | ↑ | Superoxide dismutase (MN) (EC 1.15.1.1) SOD2 | 6.83 | 21,212 |
| 1629 | | | ↑ | | Novel spectrum see table 6 | 6.15 | 25,165 |
| 1632 | TPIS | P00938 | | ↑ | Triosephosphate isomerase (EC 5.3.1.1) (TIM) TPI1 OR TPI | 6.11 | 27,492 |
| 1632 | ULA6 | P30041 | | ↑ | 24 kD protein | 6.11 | 27,492 |
| 1632 | PRCF | P40306 | | ↑ | Proteasome component MECL-1 (EC 3.4.99.46) (Macropain sub-unit MECL-1) (multicatalytic endopeptidase complex subunit MECL-1) PSMB10 OR MECL1 | 6.11 | 27,492 |
| 1664 | S85655 | P35232 | | ↓ | Prohibitin PHB | 5.44 | 27,014 |
| 1664 | HS27 | P04792 | | ↓ | Heat shock 27 kD protein (HSP 27) (Stress-responsive protein 27)(SRP27)(Estrogen-regulated 24 kD protein) (28 kD Heat shock protein) HSPB1 OR HSP27 | 5.44 | 27,014 |
| 1685 | | | | ↑ | Novel spectrum see table 6 | 4.81 | 23,690 |
| 1689 | | | | ↓ | Novel spectrum see table 6 | 4.69 | 22,974 |
| 1697 | HMG1 | P09429 | ↑ | ↑ | High mobility group protein HMG1 (HMG-1) | 4.60 | 24,122 |
| 1707 | | | ↑ | ↑ | Novel spectrum see table 6 | 6.50 | 24,673 |
| 1715 | | | ↓ | ↓ | Novel spectrum see table 6 | 5.82 | 26,369 |
| 1737 | PRC7 | P28065 | | ↑ | Proteasome chain 7 (EC 3.4.99.46) (Macropain chain 7) (Multicatalytic endopeptidase complex chain 7) (ring12 pro-tein) PSMB9 or LMP2 or RING12 | 4.56 | 19,832 |
| 1766 | | | ↓ | ↓ | Novel spectrum see table 6 | 5.61 | 17,650 |
| 1800 | | | | ↓ | Novel spectrum see table 6 | 4.47 | 17,697 |
| 1853 | B2MG | P01884 | ↑ | ↑ | Beta-2-microglobulin | 5.73 | 7,077 |
| 1861 | | G267406 | | ↓ | | 6.28 | 60,877 |
| 1902 | | | | ↑ | Novel spectrum see table 6 | 5.52 | 71,993 |
| 1923 | AMPL | P00727 | | ↑ | BOVINE Cytosol aminopeptidase (EC 3.4.11.1) (Leucine aminopeptidase) (LAP) (Leucyl aminopeptidase) (proline aminopeptidase) (EC 3.4.11.5) (prolyl aminopeptidase) See table 4 | 6.45 | 59,804 |
| 1923 | DHAC | P00352 | | ↑ | Aldehyde dehydrogenase, cyto-solic (EC 1.2.1.3) (class 1) (ALHDII) (ALDH-E1) | 6.45 | 59,804 |
| 1923 | DHE3 | P00367 | | ↑ | Glutamate dehydrogenase 1 (EC 1.4.1.3) (GDH) | 6.45 | 59,804 |
| 1930 | | | ↓ | ↓ | Novel unidentified protein | 4.73 | 47,472 |
| 1935 | | | ↑ | ↑ | Novel spectrum see table 6 | 6.51 | 49,146 |
| 1996 | ENPL | P14625 | | ↓ | Endoplasmin (94 kD Glucose-regulated protein) (grp94) (gp96 homolog) (Tumour rejec-tion antigen 1) TRA1 | 4.92 | 90,497 |
| 2036 | AMYS | P04745 | | ↑ | alpha-Amylase salivary (EC 3.2.1.1) (1,4-alpha-D-Glucan glucanohydrolase) AMY1A OR AMY1 | 6.44 | 70,123 |
| 672 | DCE2 | Q05329 | ↑ | ↑ | Glutamate decarboxylase 65 kD isoform | 4.46 | 78,008 |
| 2041 | | | ↑ | ↑ | Novel spectrum see table 6 | 6.35 | 68,704 |
| 2079 | | | ↓ | ↓ | Novel spectrum see table 6 | 5.86 | 47,814 |
| 2104 | ILEU | P30740 | | ↑ | Leukocyte elastase inhibitor (LEI) (monocyte/neutrophil elastase inhibitor) (EI) ELANH2 or PI2 | 5.37 | 41,459 |

TABLE 1-continued

HUMAN ISLET CELL PROTEINS CHARACTERISED BY MS. IDENTIFIED, IDENTIFIED BY RELATION TO ANOTHER SPECIES AND UNIDENTIFIED PROTEINS.

| Spot # | Gene Name | Identifier | Il1β 1500 | Cyt. Mix | Name Protein | Obs. pI | Mol. Wt |
|---|---|---|---|---|---|---|---|
| 2104 | 1B08 | P30463 | | ↑ | HLA class I histocompatibility antigen, BW-65(B-14) B*1402 alpha chain HLA-B or HLAB | 5.37 | 41,459 |
| 2145 | LITA | P05451 | | ↑ | (Islet cells regeneration factor)(ICRF) Lithostathine 1 alpha (Pancreatic stone protein) (PSP) Pancreatic thread protein) (PTP) | 5.38 | 13,733 |
| 2159 | ATPA | P25705 | ↑ | ↑ | ATP Synthase alpha chain, mitochondrial (EC 3.6.1.34) ATP5A1. | 6.83 | 64,414 |
| 2276 | ER60 | P30101 | | ↑ | Protein disulfide isomerase ER-60 (EC 5.3.4.1) (ERP60) (58 KD Microsomal protein) (P58) (GRP58) (ERP57) | 5.68 | 52,329 |
| 2276 | SYW | P23381 | | ↑ | Tryptophanyl-tRNA synthetase (EC 6.1.1.2) (Tryptophan-tRNA ligase) | 5.68 | 52,329 |
| 2286 | SYW | P23381 | | ↑ | Tryptophanyl-tRNA synthetase (EC 6.1.1.2) (Tryptophan-tRNA ligase) | 5.64 | 52,988 |
| 2286 | ER60 | P30101 | | ↑ | protein)(P58)(GRP58)(ERP57) | 5.64 | 52,988 |
| 2354 | | | | ↓ | Novel spectrum see table 6 | 5.75 | 44,151 |
| 2368 | ILEU | P30740 | | ↑ | Leukocyte elastase inhibitor (LEI) (monocyte/neutrophil elastase inhibitor) (EI) ELANH2 or PI2 | 5.27 | 41,658 |
| 2368 | 1B39 | P30480 | | ↑ | HLA Class I histocompatibility antigen, BW-42 B*4201 alpha chain HLA-B or HLAB | 5.27 | 41,658 |
| 2382 | | | ↓ | ↓ | Novel spectrum see table 6 | 5.74 | 36,688 |
| 2408 | | | ↑ | | Novel spectrum see table 6 | 5.74 | 29,142 |
| 2411 | | | ↑ | ↑ | Novel spectrum see table 6 | 7.17 | 21,901 |
| 2422 | | | ↑ | ↑ | Novel unidentified protein | 4.71 | 288,000 |
| 2423 | | | ↑ | ↑ | Novel unidentified protein | 4.65 | 286,000 |
| 13298 | SYW | P23381 | | ↑ | Tryptophanyl-tRNA synthetase (EC 6.1.1.2) (Tryptophan-tRNA ligase) | 5.86 | 52,288 |
| 13652 | | | | ↑ | Novel spectrum see table 6 | 4.98 | 35,726 |
| 14098 | | | | ↑ | Novel spectrum see table 6 | 6.83 | 21,691 |
| 14103 | SODM | P04179 | ↑ | ↑ | Superoxide dismutase (MN) (EC 1.15.1.1) SOD2 | 7.41 | 20,628 |

TABLE 2

HUMAN ISLET CELL PROTEINS CHARACTERISED BY MS. IDENTIFIED, IDENTIFIED RELATING TO ANOTHER SPECIES AND UNIDENTIFIED PROTEINS.

| Spot # | Gene Name | Identifier | IL1β 1500 | Cytokin Mix | Protein Name | Obs. pI | Mol. Wt |
|---|---|---|---|---|---|---|---|
| 007 | HBP | Q00341 | ↓ | | High density lipoprotein binding protein (HDL-binding protein) | 7.22 | 96,450 |
| 026 | | | | ↑ | Novel spectrum see table 7 | 8.20 | 79,860 |
| 035 | | | ↑ | ↑ | Novel spectrum see table 7 | 7.68 | 79,138 |
| 060 | | | ↓ | ↓ | Novel spectrum see table 7 | 8.34 | 72,134 |
| 076 | | | | ↑ | Novel spectrum see table 7 | 7.82 | 68,538 |
| 085 | | | | ↑ | Novel spectrum see table 7 | 7.52 | 68,772 |
| 128 | | | ↑ | | Novel spectrum see table 7 | 8.64 | 63,052 |
| 130 | | | ↑ | | Novel spectrum see table 7 | 8.43 | 64,647 |
| 140 | KPY1 | P14618 | ↑ | | Pyruvate kinase, M1 (muscle isozyme) (EC 2.7.1.40) | 8.31 | 58,557 |
| 142 | ROM | P52272 | ↓ | | Heterogeneous nuclear ribonucleoprotein M (HNRNP M) | 8.21 | 62,958 |
| 147 | ROM | P52272 | ↓ | ↓ | Heterogeneous nuclear ribonucleoprotein M (HNRNP M) | 8.03 | 62,953 |
| 147 | CPT2 | P23786 | ↓ | ↓ | Mitochondrial carnitine palmitoyltransferase II (EC 2.3.1.21) | 8.03 | 62,953 |
| 157 | PUT2 | P30038 | ↓ | ↓ | Delta-1-pyrroline-5-carboxylate dehydrogenase(EC 1.5.1.12) | 7.55 | 60,341 |
| 157 | CATA | P04040 | ↓ | ↓ | Catalase (EC 1.11.1.6) | 7.55 | 60,341 |

TABLE 2-continued

HUMAN ISLET CELL PROTEINS CHARACTERISED BY MS.
IDENTIFIED, IDENTIFIED RELATING TO ANOTHER SPECIES AND UNIDENTIFIED PROTEINS.

| Spot # | Gene Name | Identifier | IL1β 1500 | Cytokin Mix | Protein Name | Obs. pI | Mol. Wt |
|---|---|---|---|---|---|---|---|
| 167 | | Q05329 | ↑ | ↑ | Glutamate decarboxylase 65 kD isoform | 7.30 | 61,344 |
| 171 | | | ↓ | | Novel spectrum see table 7 | 7.10 | 61,058 |
| 187 | | | | ↑ | Novel spectrum see table 7 | 9.21 | 51,881 |
| 188 | | | | ↑ | Novel spectrum see table 7 | 9.17 | 51,844 |
| 195 | | | ↓ | | Novel spectrum see table 7 | 9.07 | 56,351 |
| 241 | ATPA | P25705 | ↓ | ↓ | ATP Synthase alpha chain, mitochondrial (EC 3.6.1.34) | 7.54 | 53,358 |
| 243 | | | | ↑ | Novel spectrum see table 7 | 7.55 | 55,588 |
| 247 | DHE3 | P00367 | | ↑ | Glutamate dehydrogenase 1 (EC 1.4.1.3) | 7.46 | 55,349 |
| 247 | PBEF | P43490 | | ↑ | Pre-B cell enhancing factor | 7.46 | 55,349 |
| 256 | DHE3 | P00367 | | ↑ | Glutamate dehydrogenase 1 (EC 1.4.1.3) | 6.90 | 57,118 |
| 256 | G6PD | P11413 | | ↑ | Glucose-6-phosphate 1-dehydrogenase (EC 1.1.1.49) | 6.90 | 57,118 |
| 263 | | | ↓ | ↓ | Novel unidentified protein | 9,619 | 49,828 |
| 270 | | | ↓ | | Novel spectrum see table 7 | 9.14 | 47,719 |
| 308 | GABT | P80404 | ↓ | | 4-Aminobutyrate aminotransferase, mitochondrial (EC 2.6.1.19) See table 5 | 7.96 | 51,251 |
| 339 | ODPA | P08559 | | ↑ | Pyruvate dehydrogenase E1 component, alpha subunit, somatic (EC 1.2.4.1) | 6.95 | 49,851 |
| 339 | TAP-A | Y13582 | | ↑ | Transporter associated with antigen processing subunit TAP-A | 6.95 | 49,851 |
| 339 | IDHP | P48735 | | ↑ | Isocitrate dehydrogenase (NADP), mitochondrial (EC 1.1.1.42) See table 5 | 6.95 | 49,851 |
| 369 | RAB7 | P51149 | ↑ | | RAS-Related protein RAB-7 | 8.48 | 42,835 |
| 369 | ALFA | P04075 | ↑ | | Fructose-bisphosphate aldolase A (muscle)(EC 4.1.2.13) | 8.48 | 42,835 |
| 376 | DBDD | Q04828 | ↑ | | Trans-1,2-dihydrobenzene-1,2-diol dehydrogenase (EC 1.3.1.20) | 8.14 | 41,509 |
| 376 | ALFA | P04075 | ↑ | | Fructose-bisphosphate aldolase A (muscle)(EC 4.1.2.13) | 8.14 | 41,509 |
| 377 | GAPDHG | J04038 | ↑ | | Novel unidentified protein | 8.23 | 39,510 |
| 386 | THIL | P24752 | | ↓ | Acetyl-CoA acetyltransferase, mitochondrial (EC 2.3.1.9) | 7.82 | 44,584 |
| 386 | PGK1 | P00558 | | ↓ | Phosphoglycerate kinase 1 (EC 2.7.2.3) | 7.82 | 44,584 |
| 418 | MDHP | G290614 | ↓ | | Malate dehydrogenase See table 5 | 8.89 | 35,367 |
| 418 | ROA1 | P09651 | ↓ | | Heterogeneous nuclear ribonucleoprotein A1 (Helix-destabilizing protein)(Single-strand binding protein) (HNRNP core protein A1) | 8.89 | 35,367 |
| 421 | | | ↓ | | Novel spectrum see table 7 | 8.95 | 32,958 |
| 449 | | | | ↑ | Novel spectrum see table 7 | 7.85 | 37,503 |
| 453 | POR2 | P45880 | ↓ | | Voltage-dependent anion-selective channel protein 2 (VDAC2) (Outer mitochondrial membrane protein porin) | 7.73 | 35,149 |
| 460 | NC5R | P00387 | ↓ | ↑ | NADH-cytochrome B5 reductase (EC 1.6.2.2) | 7.41 | 36,378 |
| 464 | MDHC | P40925 | ↓ | | Malate dehydrogenase, cytoplasmic (EC 1.1.1.37) | 7.01 | 36,742 |
| 474 | E123123 | E123123 | ↓ | ↓ | NIPSNAP1 protein [2769648] See table 5 | 9.44 | 25,090 |
| 500 | | | | ↑ | Novel unidentified protein | 7.85 | 30,805 |
| 508 | | | | ↑ | Novel spectrum see table 7 | 7.71 | 26,937 |
| 509 | | | ↑ | | Novel spectrum see table 7 | 7.32 | 29,812 |
| 515 | PMGB | P18669 | ↓ | | Phosphoglycerate mutase, brain (EC 5.4.2.1) | 6.86 | 25,560 |
| 517 | | | | ↑ | Novel spectrum see table 7 | 9.79 | 20,443 |
| 519 | NGAL | P80188 | | ↑ | Alpha-2-microglobulin-related subunit of MMP-9 (Lipocalin-2) | 9.55 | 20,534 |
| 532 | | | ↑ | ↑ | Novel spectrum see table 7 | 8.20 | 26,749 |

TABLE 2-continued

HUMAN ISLET CELL PROTEINS CHARACTERISED BY MS.
IDENTIFIED, IDENTIFIED RELATING TO ANOTHER SPECIES AND UNIDENTIFIED PROTEINS.

| Spot # | Gene Name | Identifier | IL1β 1500 | Cytokin Mix | Protein Name | Obs. pI | Mol. Wt |
|---|---|---|---|---|---|---|---|
| 536 | ETFB | P38117 | ↑ | | Electron transfer flavoprotein beta-subunit (beta-ETF) See table 5 | 8.11 | 26,840 |
| 536 | O14818 | O14818 | ↑ | | Proteasome subunit XAPC7 | 8.11 | 26,840 |
| 538 | TDX2 | Q06830 | ↑ | | Natural killer cell enhancing factor A | 8.02 | 21,570 |
| 538 | COF1 | P23528 | ↑ | | Cofilin, non-muscle isoform. | 8.02 | 21,570 |
| 538 | LEG3 | P17931 | ↑ | | Galectin-3 (Galactose-specific lectin 3) (MAC-2 antigen)(IGE-binding protein) (35 kd lectin) | 8.02 | 21,570 |
| 538 | SODM | P04179 | ↑ | | Superoxide dismutase (MN) (EC 1.15.1.1) | 8.02 | 21,570 |
| 544 | ES1 | P30042 | ↓ | | ES1 Protein homolog (protein KNP-I) (GT335) | 7.74 | 23,665 |
| 546 | SODM | P04179 | ↑ | ↑ | Superoxide dismutase (MN) (EC 1.15.1.1) | 7.74 | 21,122 |
| 549 | HSSOD | X07834 | ↑ | ↑ | Superoxide dismutase (MN) (EC 1.15.1.1) | 7.63 | 20,690 |
| 551 | SODM | P04179 | ↑ | ↑ | Superoxide dismutase (MN) (EC 1.15.1.1) | 7.45 | 20,108 |
| 558 | | | | ↓ | Novel spectrum see table 7 | 10.01 | 16,701 |
| 559 | | | ↓ | ↓ | Novel spectrum see table 7 | 10.06 | 16,640 |
| 560 | | | ↓ | ↓ | Novel spectrum see table 7 | 9.43 | 18,700 |
| 565 | SM22 | Q01995 | ↓ | ↓ | Smooth muscle protein 22-alpha (SM22-alpha) (Transgelin) | 8.86 | 21,594 |
| 565 | PRCE | P28074 | ↓ | ↓ | Proteasome epsilon chain (EC 3.4.99.46) | 8.86 | 21,594 |
| 568 | TDX2 | Q06830 | ↑ | | Natural killer cell enhancing factor A | 8.58 | 22,493 |
| 572 | SM2H | P37802 | | ↑ | SM22-alpha homolog (HA1756) | 8.21 | 19,370 |
| 577 | SODM | P04179 | ↑ | ↑ | Superoxide dismutase (MN) (EC 1.15.1.1). | 7.75 | 19,871 |
| 580 | | | | ↑ | Novel unidentified protein | 10.30 | 14,098 |
| 596 | COF1 | P23528 | ↓ | ↓ | Cofilin, non-muscle isoform | 8.36 | 16,170 |
| 605 | CYPH | P05092 | ↓ | ↓ | Peptidyl-prolyl cis-trans isomerase A (EC 5.2.1.8) | 7.94 | 27,866 |
| 609 | | | | ↓ | Novel spectrum see table 7 | 8.79 | 9,751 |
| 635 | Q13122 | Q13122 | ↓ | | 100 kDa coactivator See table 5 | 7.54 | 83,777 |
| 642 | GATM | P50440 | ↓ | | Glycine amidinotransferase (EC 2.1.4.1)(L-arginine: glycine amidinotransferase) | 7.15 | 51,281 |
| 642 | ENOA | P06733 | ↓ | | Alpha enolase (EC 4.2.1.11) | 7.15 | 51,281 |
| 656 | TDX2 | Q06830 | | ↑ | Thioredoxin peroxidase 2 (Thioredoxin-dependent peroxide reductase 2) (Prolifera-tion-associated protein PAG) (Natural killer cell enhancing factor A) | 8.80 | 37,605 |
| 693 | ALFA | P04075 | ↓ | ↓ | Fructose-bisphosphate aldolase A (muscle) (EC 4.1.2.13) | 9.65 | 49,829 |
| 702 | C10H | Q16181 | ↑ | | CDC10 Protein homolog | 9.15 | 46,065 |
| 719 | | | ↑ | ↑ | Novel spectrum see table 7 | 8.43 | 25,936 |
| 720 | PRCY | P28062 | ↑ | ↑ | Proteasome component C13 (EC 3.4.99.46) | 8.26 | 22,960 |
| 720 | TDX2 | Q06830 | ↑ | ↑ | Thioredoxin peroxidase 2 (Thioredoxin-dependent peroxide reductase 2) (Prolifera-tion-associated protein PAG) (Natural killer cell enhancing factor A) | 8.26 | 22,960 |
| 729 | | | ↓ | | Novel spectrum see table 7 | 7.58 | 128,532 |
| 780 | G3P2 | P04406 | | ↑ | Glyceraldehyde 3-phosphate dehydrogenase, liver (EC 1.2.1.12) | 8.02 | 39,330 |
| 780 | ROA2 | P22626 | | ↑ | Heterogeneous nuclear ribonucleoproteins A2/B1 (HNRNP A2 and HNRNP B1). | 8.02 | 39,330 |
| 786 | ANX2 | P07355 | | ↓ | Annexin II (Lipocortin II) | 7.09 | 38,665 |
| 811 | | | ↑ | | Novel unidentified protein | 8.38 | 23,437 |
| 816 | PRCE | P28074 | | ↓ | Proteasome epsilon chain (EC 3.4.99.46) | 8.97 | 21,177 |

TABLE 2-continued

HUMAN ISLET CELL PROTEINS CHARACTERISED BY MS. IDENTIFIED, IDENTIFIED RELATING TO ANOTHER SPECIES AND UNIDENTIFIED PROTEINS.

| Spot # | Gene Name | Identifier | IL1β 1500 | Cytokin Mix | Protein Name | Obs. pI | Mol. Wt |
|---|---|---|---|---|---|---|---|
| 825 | HSU889$$ | O00586 | ↑ | | hm45 | 9.58 | 15,624 |
| 828 | NDKB | P22392 | | ↓ | Nucleoside diphosphate kinase B (EC 2.7.4.6) | 8.70 | 15,409 |
| 829 | | | | ↓ | Novel spectrum see table 7 | 8.59 | 15,630 |
| 834 | CYPB | P23284 | ↓ | ↓ | Peptidyl-prolyl cis-trans isomerase B (EC 5.2.1.8) | 9.64 | 13,601 |
| 836 | | | | ↑ | Novel spectrum see table 7 | 8.19 | 20,638 |
| 837 | | | | ↑ | Novel spectrum see table 7 | 8.17 | 21,390 |
| 3755 | | | ↓ | ↓ | Novel unidentified protein | 10.56 | 12,875 |
| 3879 | | | | ↓ | Novel spectrum see table 7 | 8.35 | 16,365 |
| 3889 | FLRE | P30043 | ↑ | ↑ | Flavin reductase (EC 1.6.99.1) | 7.93 | 22,328 |
| 4325 | PRS8 | P47210 | ↓ | | 26S Protease regulatory subunit 8 (Proteasome subunit P45) (Thyroid hormone receptor interacting protein 1) (TRIP1) | 7.47 | 48,652 |
| 6600 | | | | ↑ | Novel spectrum see table 7 | 9.04 | 21,431 |

TABLE 3

PROTEINS DETECTED IN HUMAN ISLET CELL MEDIA AND CHARACTERISED BY MS IDENTIFIED AND UNIDENTIFIED PROTEINS.

| Spot # | Gene Name | Identifier | IL1β 1500 | Cytokin Mix | Protein Name | Obs. pI | Mol.Wt |
|---|---|---|---|---|---|---|---|
| 63SPI | ALBU | P02768 | ↑ | ↑ | Serum albumin ALB | 4.74 | 64,376 |
| 83SPI | ALBU | P02768 | ↑ | ↑ | Serum albumin ALB | 4.94 | 58,998 |
| 122SPI | | | ↑ | | See table 8 | 7.36 | 34,564 |
| 123SPI | | | ↓ | ↓ | See table 8 | 6.65 | 36,736 |
| 126SPI | | | ↓ | ↓ | See table 8 | 5.42 | 35,578 |
| 130SPI | | | | ↑ | See table 8 | 4.65 | 32,480 |
| 135SPI | | | | ↓ | See table 8 | 6.36 | 30,916 |
| 140SPI | | | ↓ | ↓ | See table 8 | 4.73 | 29,274 |
| 160SPI | | | | ↓ | See table 8 | 5.25 | 21,101 |
| 168SPI | ALBU | P02768 | ↓ | | Serum albumin ALB | 5.27 | 18,521 |
| 213SPI | ALBU | P02768 | | ↑ | Serum albumin ALB | 5.88 | 31,124 |
| 215SPI | ALBU | P02768 | | ↓ | Serum albumin ALB | 4.98 | 12,7138 |
| 215SPI | TRFE | P02787 | | ↓ | Serotransferrin (Siderophilin) (beta-1-Metal binding globulin) TF | 4.98 | 12,7138 |
| 218SPI | | | | | See table 8 | 6.27 | 632,16 |
| 248SPI | | | ↓ | ↓ | See table 8 | 4.67 | 292,24 |
| 258SPI | ALBU | P02768 | | ↑ | Serum albumin ALB | 6.15 | 246,493 |
| 258SPI | HSIG G1LH | Y14737 | | ↑ | Immunoglobulin lambda heavy chain | 6.15 | 246,493 |
| 277SPI | | | ↓ | ↓ | See table 8 | 5.05 | 15,752 |
| 304SPI | | | ↓ | ↓ | See table 8 | 6.71 | 36,953 |
| 314SPI | | | | ↑ | See table 8 | 6.46 | 56,100 |
| 320SPI | ALBU | P02768 | ↓ | | Serum albumin ALB | 5.89 | 9,210 |
| 338SPI | | | ↓ | ↓ | See table 8 | 4.67 | 16,603 |
| 1157SPI | ALBU | P02768 | ↓ | ↓ | Serum albumin ALB | 5.47 | 18,501 |
| 1157SPI | HSIG G1LH | Y14737 | ↓ | ↓ | Immunoglobulin lambda heavy chain | 5.47 | 18,501 |

TABLE 4

HUMAN ISLET CELL PROTEINS CHARACTERISED BY MS

The peptide molecular weight values are read directly out of the mass spectrometer and are thus associated with the accuracies normally obtained with such instrumentation. These mass values are from human islet cell proteins recovered from the IEF gels and have been identified by reference to proteins from other species, recorded in publicly available databases (whether nucleotide or protein sequence).

IEF spot 724:

| | | | | | | |
|---|---|---|---|---|---|---|
| 984.4406 | 1004.6172 | 1045.5750 | 1084.6248 | 1137.5220 | 1172.5513 | 1181.5787 |
| 1188.5267 | 1189.5705 | 1193.5450 | 1209.5364 | 1232.6502 | 1237.5782 | 1244.6390 |

TABLE 4-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the IEF gels and
have been identified by reference to proteins from other species, recorded in publicly
available databases (whether nucleotide or protein sequence).

| | | | | | | |
|---|---|---|---|---|---|---|
| 1273.6111 | 1365.6163 | 1381.6246 | 1418.7151 | 1434.7000 | 1437.7885 | 1476.6972 |
| 1525.7884 | 1544.7837 | 1583.7063 | 1589.8061 | 1601.7708 | 1618.7619 | 1630.8195 |
| 1645.8241 | 1684.8527 | 1700.7857 | 1728.8839 | 1730.8908 | 1745.9084 | 1781.8147 |
| 1794.8168 | 1826.8641 | 1860.9918 | 1918.9139 | 1940.9287 | 1989.9645 | 2005.9335 |
| 2055.9358 | 2077.1362 | 2095.9846 | 2211.0999 | 2328.1808 | 2674.4376 | 3198.8492 |

IEF spot 963:

| | | | | | | |
|---|---|---|---|---|---|---|
| 903.5003 | 976.5949 | 1045.5749 | 1064.5752 | 1168.5158 | 1198.6904 | 1319.6604 |
| 1341.6072 | 1350.6473 | 1379.6844 | 1437.8828 | 1445.7037 | 1501.7661 | 1509.6583 |
| 1515.7456 | 1596.7730 | 1707.7736 | 1790.9116 | 1794.8513 | 1797.8409 | 1808.9138 |
| 1838.9222 | 1852.9407 | 1878.9424 | 1946.9897 | 2122.0285 | 2150.0260 | 2211.0999 |
| 2406.2399 | 2559.1687 | 2585.3182 | | | | |

IEF spot 977:

| | | | | | | |
|---|---|---|---|---|---|---|
| 842.5100 | 973.4918 | 1021.4022 | 1031.4738 | 1037.3794 | 1045.4938 | 1060.7676 |
| 1075.5956 | 1151.6148 | 1159.5482 | 1179.5398 | 1196.5457 | 1263.5613 | 1267.6112 |
| 1277.6170 | 1279.5629 | 1307.5846 | 1320.5246 | 1329.5717 | 1386.6334 | 1437.7641 |
| 1458.6907 | 1472.6424 | 1475.6892 | 1536.8279 | 1597.8518 | 1674.8387 | 1700.9337 |
| 1717.7814 | 1794.8163 | 1802.9448 | 1826.7513 | 1873.0013 | 1881.0435 | 1888.9044 |
| 1942.0398 | 1994.0735 | 2211.0999 | 2225.1090 | 2231.1803 | 2455.2958 | |

IEF spot 1421:

| | | | | | | |
|---|---|---|---|---|---|---|
| 957.5447 | 1053.4829 | 1075.5106 | 1114.5114 | 1146.5867 | 1151.6223 | 1163.5530 |
| 1177.5601 | 1197.6195 | 1222.5030 | 1227.5776 | 1277.6330 | 1291.6297 | 1302.6520 |
| 1307.6147 | 1317.6238 | 1327.6099 | 1343.6147 | 1383.6003 | 1391.6233 | 1393.6514 |
| 1396.7482 | 1403.6989 | 1421.6244 | 1427.8312 | 1434.6764 | 1439.7253 | 1460.6249 |
| 1469.7214 | 1475.6805 | 1477.6583 | 1487.7037 | 1489.6919 | 1515.7063 | 1540.7410 |
| 1542.7700 | 1544.7626 | 1565.7587 | 1570.7737 | 1588.7486 | 1613.8336 | 1619.8079 |
| 1630.8408 | 1639.7890 | 1645.7757 | 1650.8568 | 1674.8047 | 1678.8083 | 1685.7486 |
| 1694.8735 | 1701.7636 | 1726.8556 | 1741.8646 | 1749.8863 | 1763.7788 | 1789.9034 |
| 1805.8828 | 1837.9159 | 1850.9476 | 1863.9118 | 1869.9458 | 1923.9277 | 1938.8968 |
| 1988.0785 | 1993.9638 | 2052.0445 | 2101.0154 | 2139.0677 | 2155.0785 | 2175.8964 |
| 2196.1696 | 2211.1000 | 2225.1153 | 2230.0816 | 2444.2075 | 2461.1385 | |

IEF spot 1861:

| | | | | | | |
|---|---|---|---|---|---|---|
| 986.6183 | 1099.5910 | 1277.6498 | 1305.6530 | 1383.6670 | 1390.5687 | 1462.7108 |
| 1475.7014 | 1489.7417 | 1516.7727 | 1544.7517 | 1555.7811 | 1590.7901 | 1594.8311 |
| 1638.7729 | 1644.8520 | 1654.8019 | 1661.7714 | 1701.8654 | 1707.7328 | 1716.8788 |
| 1746.9048 | 1756.9955 | 1794.8406 | 1799.9569 | 1802.8989 | 1837.9500 | 1851.9245 |
| 1900.9804 | 1920.1066 | 1990.9681 | 1993.9618 | 2062.0419 | 2211.1082 | 2225.1014 |
| 2272.1417 | 2298.1959 | 2472.2712 | 2502.2031 | | | |

IEF spot 1923:

| | | | | | | |
|---|---|---|---|---|---|---|
| 1004.6256 | 1045.5750 | 1084.6033 | 1137.4897 | 1172.5717 | 1181.5737 | 1188.5163 |
| 1189.5777 | 1193.5510 | 1209.5453 | 1232.6509 | 1237.5933 | 1263.6638 | 1273.6130 |
| 1277.6849 | 1307.6799 | 1365.6431 | 1381.6188 | 1394.7306 | 1418.7243 | 1425.6424 |
| 1437.8278 | 1444.6997 | 1455.7280 | 1475.7475 | 1525.7932 | 1544.7815 | 1583.7130 |
| 1589.7876 | 1601.7387 | 1618.7568 | 1630.8242 | 1645.8190 | 1669.8494 | 1684.8860 |
| 1686.8789 | 1700.8011 | 1707.8472 | 1728.8715 | 1737.8908 | 1746.8984 | 1748.9094 |
| 1779.9697 | 1782.8774 | 1794.8152 | 1835.9384 | 1838.9265 | 1860.9665 | 1908.0260 |
| 1915.9525 | 1920.9264 | 1940.9263 | 1989.9395 | 2055.9253 | 2077.1037 | 2095.9638 |
| 2211.0999 | 2278.2563 | 2328.1495 | 3197.5962 | 3494.9900 | | |

TABLE 5

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the NEPHGE gels
and have been identified by reference to proteins from other species, recorded in
publically available databases (whether nucleotide or protein sequence).

NEPHGE spot 308:

| | | | | | | |
|---|---|---|---|---|---|---|
| 1016.5065 | 1032.4876 | 1035.6038 | 1055.5031 | 1148.5696 | 1179.6000 | 1197.6175 |
| 1211.5699 | 1221.5578 | 1229.7271 | 1264.6730 | 1265.6893 | 1277.6546 | 1283.7385 |
| 1307.6327 | 1317.7154 | 1338.7857 | 1352.8162 | 1379.7060 | 1383.6587 | 1405.6557 |
| 1434.7509 | 1475.7249 | 1487.7638 | 1505.7494 | 1527.6946 | 1539.7651 | 1549.7666 |
| 1561.7328 | 1594.8652 | 1612.7713 | 1628.7452 | 1631.7017 | 1636.6749 | 1638.8614 |

TABLE 5-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the NEPHGE gels
and have been identified by reference to proteins from other species, recorded in
publically available databases (whether nucleotide or protein sequence).

| | | | | | | |
|---|---|---|---|---|---|---|
| 1645.8028 | 1707.7680 | 1710.8218 | 1719.7991 | 1757.9016 | 1770.9237 | 1786.9209 |
| 1794.8343 | 1812.9308 | 1822.9402 | 1837.9966 | 1852.9594 | 1940.9424 | 1988.0063 |
| 1993.9935 | 2064.1358 | 2149.0169 | 2155.2298 | 2196.1764 | 2211.0999 | 2250.1119 |
| 2596.2598 | 2674.3040 | 3150.8016 | | | | |

NEPHGE spot 339:

| | | | | | | |
|---|---|---|---|---|---|---|
| 1009.3940 | 1171.5822 | 1179.5496 | 1226.4567 | 1277.6437 | 1320.6468 | 1383.6308 |
| 1405.4537 | 1411.7060 | 1426.7141 | 1437.8630 | 1471.7116 | 1475.7304 | 1483.6959 |
| 1493.6772 | 1501.7870 | 1542.8788 | 1592.6512 | 1596.7767 | 1638.8489 | 1695.8217 |
| 1707.7969 | 1715.8272 | 1778.8540 | 1794.8041 | 1797.8152 | 1819.8835 | 1823.9229 |
| 1838.9469 | 1851.9609 | 1878.9472 | 1940.9953 | 1962.8823 | 1978.9525 | 1993.9931 |
| 2018.0026 | 2211.1201 | 2225.1558 | 2274.1434 | 2283.1658 | 2299.2521 | 2344.3761 |
| 2383.9712 | 2402.2620 | 2406.3035 | 2431.0818 | 2705.2697 | 2719.1012 | 2731.3472 |
| 2807.4831 | | | | | | |

NEPHGE spot 418:

| | | | | | | |
|---|---|---|---|---|---|---|
| 822.4000 | 832.4732 | 842.5100 | 908.6270 | 928.4098 | 992.4582 | 1033.4602 |
| 1045.4933 | 1065.4224 | 1073.4967 | 1107.4692 | 1116.4852 | 1147.5546 | 1157.4959 |
| 1165.4439 | 1167.4800 | 1179.5001 | 1201.5553 | 1218.5409 | 1232.5022 | 1277.6204 |
| 1299.5559 | 1307.5788 | 1352.6447 | 1357.6185 | 1384.6983 | 1393.6325 | 1406.5687 |
| 1422.5837 | 1427.6627 | 1437.6719 | 1454.6286 | 1470.6347 | 1475.6829 | 1493.6574 |
| 1500.6009 | 1503.6764 | 1560.7424 | 1628.7381 | 1657.7530 | 1694.6866 | 1699.7547 |
| 1707.7213 | 1716.8199 | 1741.7043 | 1751.7916 | 1784.8936 | 1791.7001 | 1838.8855 |
| 1851.8301 | 1867.8840 | 1987.9418 | 2211.0999 | 2365.2112 | 2383.9402 | |

NEPHGE spot 474:

| | | | | | | |
|---|---|---|---|---|---|---|
| 679.5296 | 706.4771 | 714.4944 | 730.4229 | 991.5260 | 1012.5126 | 1092.5579 |
| 1108.5016 | 1212.5737 | 1225.5337 | 1277.6968 | 1307.6588 | 1446.8720 | 1475.7748 |
| 1604.7245 | 1710.9075 | 1772.9576 | 1788.9636 | 1794.8920 | 1867.0268 | 2018.1137 |
| 2174.2120 | 2211.2344 | 2401.4191 | 2789.6777 | | | |

NEPHGE spot 536:

| | | | | | | |
|---|---|---|---|---|---|---|
| 853.5924 | 945.5755 | 978.5561 | 998.5303 | 1011.6255 | 1045.5785 | 1054.6595 |
| 1066.5559 | 1102.5904 | 1179.6000 | 1183.7368 | 1184.6987 | 1277.6972 | 1291.7293 |
| 1295.7841 | 1304.7071 | 1307.7127 | 1339.7158 | 1403.7144 | 1617.8575 | 1634.8604 |
| 1664.8766 | 1666.7879 | 1683.9517 | 1737.8633 | 1794.8280 | 1801.8590 | 1812.0373 |
| 1902.8723 | 1907.8546 | 1918.9088 | 1940.9273 | 1945.9582 | 1993.9928 | 2026.0434 |
| 2065.0661 | 2196.0354 | 2211.0999 | 2449.2132 | 2577.3710 | | |

NEPHGE spot 635,

| | | | | | | |
|---|---|---|---|---|---|---|
| 842.5456 | 1011.6439 | 1036.5530 | 1045.5684 | 1048.6357 | 1064.5920 | 1071.5091 |
| 1082.6031 | 1092.5681 | 1106.6437 | 1157.5750 | 1179.6000 | 1232.6820 | 1277.7070 |
| 1307.6714 | 1314.7441 | 1320.5891 | 1323.6417 | 1338.7554 | 1350.6851 | 1357.6931 |
| 1383.6509 | 1389.6969 | 1396.6928 | 1401.6416 | 1407.7207 | 1429.6767 | 1434.7677 |
| 1461.6809 | 1475.7583 | 1493.7287 | 1535.8219 | 1620.8873 | 1638.8669 | 1657.7833 |
| 1665.9997 | 1702.8599 | 1707.7849 | 1709.8196 | 1716.8613 | 1724.9400 | 1757.9150 |
| 1794.8189 | 1829.8908 | 1838.9142 | 1851.9404 | 1867.9269 | 1940.9311 | 1959.9202 |
| 1993.9642 | 2047.0784 | 2150.0418 | 2211.0999 | | | |

TABLE 6

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the IEF gels and do
not match any protein recorded in publically available databases (whether nucleotide or
protein sequence).

IEF spot 8:

| | | | | | | |
|---|---|---|---|---|---|---|
| 1045.6833 | 1179.6990 | 1277.8454 | 1475.8751 | 1794.9853 | 1816.9418 | 1833.9383 |
| 2211.3200 | 2225.3308 | 2231.4079 | 2239.3200 | 2249.2374 | 2298.4052 | 2721.5682 |
| 2807.6137 | 3340.0959 | | | | | |

IEF spot 370:

| | | | | | | |
|---|---|---|---|---|---|---|
| 842.5100 | 995.5638 | 1009.5700 | 1023.5915 | 1045.4798 | 1155.5365 | 1254.5757 |
| 1264.5343 | 1275.5888 | 1348.5604 | 1419.6498 | 1475.6669 | 1794.7643 | 1940.9135 |
| 1950.0052 | 1993.9562 | 2211.0999 | 2403.2608 | | | |

TABLE 6-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the IEF gels and do
not match any protein recorded in publicly available databases (whether nucleotide or
protein sequence).

IEF spot 473:

| | | | | | | |
|---|---|---|---|---|---|---|
| 1008.2678 | 1094.4059 | 1151.4450 | 1208.4057 | 1254.4806 | 1267.4619 | 1277.4823 |
| 1285.4220 | 1315.4963 | 1355.4978 | 1375.5110 | 1383.4741 | 1475.5626 | 1488.6075 |
| 1497.5317 | 1506.5091 | 1555.6522 | 1589.7591 | 1607.6268 | 1615.6441 | 1624.6694 |
| 1668.7791 | 1697.7066 | 1700.8164 | 1706.8476 | 1716.7516 | 1761.7701 | 1794.7184 |
| 1826.7320 | 1838.8344 | 1853.8072 | 1880.9486 | 1919.9092 | 1922.8662 | 1940.8495 |
| 1993.9770 | 2034.9080 | 2107.0836 | 2211.0999 | 2225.1068 | 2231.2066 | |

IEF spot 524:

| | | | | | | |
|---|---|---|---|---|---|---|
| 842.5100 | 1045.5152 | 1201.6168 | 1404.6128 | 1481.7153 | 1561.8987 | 1794.7933 |
| 1826.8585 | 1940.9415 | 2211.0999 | 2225.1233 | 2230.1675 | 2240.1371 | 2284.2128 |
| 2298.2138 | 2315.1913 | | | | | |

IEF spot 535:

| | | | | | | |
|---|---|---|---|---|---|---|
| 1061.3738 | 1077.1038 | 1277.6330 | 1352.6221 | 1398.7634 | 1470.7513 | 1561.2142 |
| 1561.6867 | 1637.8923 | 1670.3631 | 1674.8225 | 1794.8100 | 1826.8587 | 1838.9166 |
| 1852.9038 | 1940.9301 | 1942.9249 | 1993.9472 | 2027.0373 | 2083.0422 | 2085.0098 |
| 2914.5719 | | | | | | |

IEF spot 551:

| | | | | | | |
|---|---|---|---|---|---|---|
| 973.6111 | 1036.5433 | 1109.4879 | 1179.6000 | 1211.6334 | 1263.7032 | 1277.7166 |
| 1308.6403 | 1352.5835 | 1365.6650 | 1369.6804 | 1383.6823 | 1434.7299 | 1475.7586 |
| 1487.7383 | 1493.7134 | 1637.9332 | 1687.8217 | 1699.8350 | 1707.7806 | 1716.8403 |
| 1784.7226 | 1794.8425 | 1796.9945 | 1838.0168 | 1993.9891 | 2211.1000 | 2297.1887 |
| 2663.2473 | 2705.1573 | 2720.2757 | 2807.3089 | 3121.4704 | | |

IEF spot 651:

| | | | | | | |
|---|---|---|---|---|---|---|
| 842.5100 | 1263.6624 | 1277.6589 | 1332.6843 | 1404.7025 | 1419.6938 | 1491.7324 |
| 1508.9459 | 1512.7036 | 1517.8358 | 1587.8030 | 1638.8522 | 1729.9886 | 1749.0137 |
| 1794.8426 | 1838.9400 | 1844.0229 | 1851.9611 | 1922.9308 | 1934.0288 | 1940.9595 |
| 1987.0910 | 1993.9490 | 2000.0800 | 2040.1006 | 2043.1000 | 2083.9484 | 2093.0841 |
| 2124.0855 | 2137.1187 | 2165.0434 | 2211.1000 | 2225.1111 | 2231.1652 | 2284.1895 |
| 2298.2321 | | | | | | |

IEF spot 656:

| | | | | | | |
|---|---|---|---|---|---|---|
| 842.5100 | 1045.5397 | 1176.4935 | 1179.5345 | 1277.6399 | 1307.6511 | 1320.5211 |
| 1323.6361 | 1354.6520 | 1357.6312 | 1383.5951 | 1433.7019 | 1450.6642 | 1461.6939 |
| 1473.6322 | 1475.7114 | 1498.5909 | 1561.6855 | 1613.7589 | 1707.7832 | 1716.8349 |
| 1718.8505 | 1794.7881 | 1838.9436 | 1854.6243 | 1882.0321 | 1908.9185 | 1992.0052 |
| 1993.9823 | 2130.2472 | 2211.0999 | 2225.0997 | 2284.1469 | 2298.1604 | |

IEF spot 909:

| | | | | | | |
|---|---|---|---|---|---|---|
| 842.5100 | 1045.5307 | 1066.0095 | 1077.1195 | 1140.5949 | 1151.6268 | 1173.5611 |
| 1179.5166 | 1234.5855 | 1263.6313 | 1277.6287 | 1301.6433 | 1307.6049 | 1314.6572 |
| 1320.5066 | 1357.6246 | 1383.5860 | 1434.6890 | 1475.6862 | 1493.6750 | 1532.7323 |
| 1535.8087 | 1547.6337 | 1623.8526 | 1638.7999 | 1669.8425 | 1707.7065 | 1716.8138 |
| 1739.9255 | 1766.8347 | 1791.7279 | 1794.7902 | 1806.8742 | 1838.9270 | 1852.9250 |
| 1868.9303 | 1881.0355 | 1890.9128 | 1940.9064 | 1944.9914 | 1993.9906 | 2111.9138 |
| 2171.1384 | 2211.1000 | 2225.1044 | 2230.1917 | 2240.1803 | 2298.1557 | 2384.9693 |

IEF spot 1013:

| | | | | | | |
|---|---|---|---|---|---|---|
| 842.5100 | 918.2719 | 995.6119 | 1045.5322 | 1050.5029 | 1144.5461 | 1191.6716 |
| 1201.6286 | 1214.5566 | 1308.4854 | 1319.6821 | 1341.5464 | 1474.7240 | 1536.8891 |
| 1604.7969 | 1701.9124 | 1707.8899 | 1781.8221 | 1794.8021 | 1801.0348 | 1826.8456 |
| 1916.8642 | 1923.9753 | 1940.9620 | 1982.9495 | 1999.9878 | 2083.9889 | 2112.0200 |
| 2211.0999 | 2225.1149 | 2314.1955 | | | | |

IEF spot 1186:

| | | | | |
|---|---|---|---|---|
| 842.5100 | 1277.6348 | 1795.8217 | 1918.9837 | 2211.1000 |

IEF spot 1353:

| | | | | | | |
|---|---|---|---|---|---|---|
| 842.5100 | 870.5290 | 944.4994 | 981.5298 | 989.5240 | 995.5611 | |
| 998.5569 | 1009.5790 | 1023.5824 | 1035.4838 | 1045.5007 | 1111.4667 | 1172.5993 |
| 1179.5128 | 1198.5672 | 1240.5947 | 1263.5655 | 1277.6049 | 1307.5663 | 1314.6804 |
| 1411.6442 | 1421.5773 | 1427.7229 | 1460.6109 | 1475.6725 | 1533.7745 | 1542.7685 |
| 1544.7350 | 1614.8168 | 1699.7857 | 1707.7142 | 1716.8069 | 1763.7734 | 1794.7732 |
| 1940.9113 | 1993.9414 | 2082.9974 | 2211.0999 | 2284.1656 | 2298.1924 | 2315.1733 |
| 2346.2393 | 2402.2586 | | | | | |

TABLE 6-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the IEF gels and do
not match any protein recorded in publicly available databases (whether nucleotide or
protein sequence).

IEF spot 1400:

| | | | | | |
|---|---|---|---|---|---|
| 1077.4235 | 1545.1665 | 1557.1800 | 1615.2899 | 1629.3171 | 1639.2424 | 1644.2703 |
| 1650.2177 | 1679.2655 | 1764.2349 | 1781.2559 | 1795.2691 | 1827.3200 | 1923.3377 |
| 1941.4215 | 2012.4217 | 2084.4777 | 2196.6995 | 2211.6313 | 2298.7533 | 2314.7422 |

IEF spot 1477:

| | | | | | | |
|---|---|---|---|---|---|---|
| 842.5100 | 1045.5856 | 1061.4107 | 1201.6810 | 1243.6338 | 1298.7593 | 1314.7386 |
| 1353.7389 | 1442.6934 | 1794.8225 | 1816.8090 | 1826.8278 | 1940.9308 | 1962.9235 |
| 2083.9815 | 2211.0999 | 2225.0952 | 2233.0880 | 2239.1110 | 2247.1584 | 2259.1687 |
| 2283.1243 | 2298.1830 | 2300.1578 | 2300.1578 | 2314.2315 | 842.5100 | |

IEF spot 1549:

| | | | | | | |
|---|---|---|---|---|---|---|
| 944.5832 | 952.5302 | 963.4854 | 968.5148 | 989.6031 | 1011.4641 | 1038.5338 |
| 1045.5750 | 1085.6121 | 1109.5172 | 1123.4616 | 1141.4897 | 1151.5241 | 1169.4984 |
| 1180.5681 | 1239.5897 | 1254.5633 | 1263.6304 | 1293.6086 | 1332.6938 | 1404.7182 |
| 1449.7184 | 1453.7806 | 1462.6382 | 1481.7035 | 1487.7197 | 1504.7506 | 1534.7408 |
| 1550.6930 | 1601.8160 | 1620.7593 | 1696.8256 | 1776.8086 | 1794.8104 | 1834.9544 |
| 2082.9407 | 2104.9489 | 2120.9161 | 2191.1179 | 2211.0999 | 2307.1286 | 3494.7356 |

IEF spot 1629:

| | | | | | | |
|---|---|---|---|---|---|---|
| 842.5100 | 1081.5213 | 1163.5498 | 1277.6486 | 1510.6347 | 1602.8306 | 1614.7873 |
| 1622.7896 | 1766.8741 | 1783.9029 | 1794.8229 | 1821.9804 | 1889.0158 | 1905.9656 |
| 1940.9499 | 1994.9698 | 2001.0446 | 2015.9908 | 2100.9779 | 2194.1209 | 2206.0567 |
| 2211.1000 | 2222.1179 | 2227.0998 | 2232.1773 | 2239.1005 | 2284.1852 | 2298.1724 |
| 2315.1713 | 2402.2609 | | | | | |

IEF spot 1685:

| | | | | | | |
|---|---|---|---|---|---|---|
| 842.5100 | 1022.5918 | 1041.4846 | 1045.5657 | 1081.5660 | 1094.6393 | 1123.5216 |
| 1140.6257 | 1151.6597 | 1179.5806 | 1198.6117 | 1237.5847 | 1251.7101 | 1258.6385 |
| 1264.6728 | 1267.6759 | 1277.6951 | 1294.6699 | 1311.6514 | 1337.5819 | 1360.6477 |
| 1367.6365 | 1375.7053 | 1424.7336 | 1475.7213 | 1496.7138 | 1510.6506 | 1535.8694 |
| 1555.7990 | 1589.9143 | 1613.8034 | 1624.8305 | 1664.9408 | 1668.8845 | 1700.9492 |
| 1717.9895 | 1761.8855 | 1765.8807 | 1781.9631 | 1794.8734 | 1881.0306 | 1940.9391 |
| 1994.0829 | 2015.9654 | 2076.0592 | 2107.1025 | 2211.0999 | 2225.0950 | 2240.1006 |
| 2292.0774 | 2298.1665 | | | | | |

IEF spot 1689:

| | | | | | | |
|---|---|---|---|---|---|---|
| 1151.6236 | 1252.6359 | 1264.6176 | 1277.6329 | 1307.6662 | 1341.7101 | 1344.6395 |
| 1368.5754 | 1375.6627 | 1383.6225 | 1394.6589 | 1419.6925 | 1497.7909 | 1509.7184 |
| 1535.8266 | 1555.7803 | 1566.7852 | 1570.8423 | 1578.7812 | 1585.8527 | 1613.8076 |
| 1621.7580 | 1650.8802 | 1707.7462 | 1712.7774 | 1715.8487 | 1728.8015 | 1794.7926 |
| 1804.8966 | 1818.9066 | 1825.8959 | 1838.8990 | 1881.0462 | 1895.9270 | 1936.9580 |
| 1952.9601 | 1962.9766 | 1980.9366 | 2082.9915 | 2099.0082 | 2139.9269 | 2155.9884 |
| 2196.2051 | 2211.0999 | 2225.1098 | 2239.1133 | 2283.1903 | 2314.2017 | 2362.0761 |
| 2528.2225 | | | | | | |

IEF spot 1707:

| | | | | | | |
|---|---|---|---|---|---|---|
| 842.5100 | 1187.5823 | 1277.6596 | 1306.7072 | 1383.6581 | 1424.7845 | 1475.7350 |
| 1481.8440 | 1560.7928 | 1589.8204 | 1612.7670 | 1647.8648 | 1708.8533 | 1743.8693 |
| 1794.8108 | 1826.7289 | 1940.9432 | 1993.9578 | 2020.0073 | 2034.9747 | 2083.9911 |
| 2211.1000 | | | | | | |

IEF spot 1715:

| | | | | | | |
|---|---|---|---|---|---|---|
| 842.5100 | 995.5831 | 1009.5829 | 1023.5820 | 1045.5202 | 1070.4854 | 1087.5118 |
| 1154.6259 | 1314.6766 | 1316.5599 | 1370.6312 | 1427.7708 | 1593.7765 | 1675.7657 |
| 1713.7559 | 1794.7779 | 1900.9901 | 1940.9405 | 1981.9982 | 2211.0999 | 2225.0993 |
| 2230.1190 | 2239.1017 | 2353.1943 | 2447.2427 | 2455.3168 | 2465.3108 | 2664.2730 |
| 2721.2672 | | | | | | |

IEF spot 1766:

| | | | | | | |
|---|---|---|---|---|---|---|
| 842.5100 | 944.4946 | 989.5409 | 1017.6835 | 1032.5402 | 1045.5083 | 1060.5038 |
| 1071.5384 | 1077.0911 | 1084.5774 | 1107.4665 | 1129.5720 | 1179.5248 | 1193.5853 |
| 1201.5667 | 1205.5819 | 1234.6034 | 1263.6062 | 1277.6315 | 1281.5339 | 1314.7075 |
| 1320.5393 | 1325.6773 | 1349.6438 | 1363.6477 | 1381.7550 | 1398.6787 | 1407.6259 |
| 1434.7108 | 1436.6620 | 1475.7174 | 1491.8240 | 1493.6869 | 1505.8475 | 1519.8568 |
| 1556.8407 | 1602.7688 | 1636.8141 | 1678.8399 | 1707.7623 | 1743.8024 | 1780.7768 |
| 1794.7887 | 1838.9008 | 1872.9419 | 1931.1324 | 1993.9690 | 2083.0147 | 2097.9525 |
| 2211.1000 | 3451.8065 | | | | | |

TABLE 6-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the IEF gels and do
not match any protein recorded in publicly available databases (whether nucleotide or
protein sequence).

IEF spot 1800:

| | | | | | |
|---|---|---|---|---|---|
| 842.5100 | 965.4350 | 976.4934 | 992.4239 | 1045.5079 | 1065.4919 | 1074.4756 |
| 1120.5483 | 1164.5137 | 1179.5419 | 1254.6347 | 1260.5475 | 1277.6344 | 1292.6279 |
| 1302.6309 | 1308.6085 | 1383.6186 | 1415.5896 | 1419.6711 | 1434.7317 | 1467.8188 |
| 1475.7193 | 1487.7064 | 1493.6788 | 1506.7180 | 1522.7029 | 1524.6992 | 1553.6528 |
| 1639.8495 | 1657.7832 | 1665.7380 | 1676.7759 | 1681.7378 | 1707.7739 | 1709.7370 |
| 1716.8454 | 1759.9521 | 1783.7564 | 1791.8506 | 1794.8215 | 1838.9510 | 1940.9262 |
| 1993.9821 | 2211.1000 | 2671.4041 | 2687.4419 | 2721.3115 | | |

IEF spot 1902:

| | | | | | |
|---|---|---|---|---|---|
| 1045.5319 | 1352.5423 | 1794.7875 | 1942.9269 | 2211.0737 | 2225.0935 | 2230.1477 |
| 2240.0732 | 2285.1071 | 2298.1320 | 2315.1105 | | | |

IEF spot 1935:

| | | | | | |
|---|---|---|---|---|---|
| 842.5100 | 976.5614 | 995.5965 | 1045.5409 | 1137.6845 | 1277.6514 | 1320.6409 |
| 1411.7267 | 1437.8481 | 1445.6587 | 1463.6928 | 1475.7462 | 1515.7311 | 1540.7581 |
| 1592.7102 | 1794.8039 | 1878.9334 | 1940.9419 | 1993.9565 | 2211.0999 | 2225.1032 |
| 2230.2255 | 2239.1103 | 2284.2093 | 2293.1057 | 2298.2019 | 2406.2187 | |

IEF spot 2041:

| | | | | | |
|---|---|---|---|---|---|
| 842.5100 | 870.5188 | 995.5983 | 1009.5573 | 1011.5865 | 1045.5044 | 1073.4231 |
| 1253.5788 | 1277.6266 | 1287.5708 | 1357.6107 | 1391.6701 | 1427.6972 | 1475.7224 |
| 1487.7416 | 1567.7156 | 1567.7156 | 1615.7750 | 1624.7871 | 1715.8582 | 1745.9047 |
| 1794.7998 | 1826.7704 | 1940.9130 | 1993.9553 | 2011.9662 | 2082.9776 | 2211.0999 |
| 2298.1935 | | | | | | |

IEF spot 2079:

| | | | | | |
|---|---|---|---|---|---|
| 842.5100 | 1045.5126 | 1074.5097 | 1128.4836 | 1144.4893 | 1179.5318 | 1201.6130 |
| 1215.4643 | 1226.5814 | 1232.5216 | 1267.6287 | 1272.5458 | 1277.6236 | 1291.6468 |
| 1314.6885 | 1320.5261 | 1330.5987 | 1350.6193 | 1475.6943 | 1535.8375 | 1553.7165 |
| 1624.8774 | 1649.7828 | 1657.7624 | 1664.9078 | 1687.9333 | 1707.7469 | 1791.7278 |
| 1794.8045 | 1813.8890 | 1826.7495 | 1838.9154 | 1851.9083 | 1940.8912 | 1970.0934 |
| 1991.1016 | 2096.9820 | 2150.0510 | 2198.9812 | 2211.0999 | 2225.1041 | 2230.2625 |
| 2239.1553 | 2246.2206 | 2314.1744 | 2338.1612 | 2367.2374 | 2383.9340 | 2501.2666 |
| 2617.5910 | 3121.5635 | 3126.5388 | | | | |

IEF spot 2354:

| | | | | | |
|---|---|---|---|---|---|
| 842.5100 | 870.4939 | 1012.5286 | 1022.5067 | 1029.3960 | 1045.4719 | 1056.5117 |
| 1073.4775 | 1081.4615 | 1090.4351 | 1094.5511 | 1102.4539 | 1128.4784 | 1140.5488 |
| 1151.5872 | 1157.5311 | 1179.4996 | 1191.5849 | 1194.5774 | 1198.5323 | 1234.5742 |
| 1251.6062 | 1259.5414 | 1263.5214 | 1267.6025 | 1273.4958 | 1277.5635 | 1300.4431 |
| 1307.5481 | 1313.6037 | 1320.4906 | 1340.5876 | 1364.6104 | 1364.6104 | 1375.6429 |
| 1383.5667 | 1388.6014 | 1402.6673 | 1434.6889 | 1474.6751 | 1493.6490 | 1496.6232 |
| 1535.8077 | 1555.7629 | 1577.6201 | 1604.7703 | 1613.7706 | 1664.8756 | 1667.8486 |
| 1692.8624 | 1707.7665 | 1716.7989 | 1735.7390 | 1777.9508 | 1781.8353 | 1794.7863 |
| 1804.9251 | 1825.6777 | 1838.8740 | 1851.8978 | 1881.0424 | 1889.9527 | 1910.9100 |
| 1916.8051 | 1940.8769 | 1966.0780 | 1982.9535 | 1991.0975 | 1994.0892 | 2076.0763 |
| 2112.0231 | 2211.0999 | 2225.1186 | 2230.1505 | 2239.1165 | 2283.1613 | 2292.1405 |
| 2297.1707 | | | | | | |

IEF spot 2382:

| | | | | | |
|---|---|---|---|---|---|
| 792.5768 | 810.5959 | 814.6006 | 824.2747 | 830.5626 | 842.5100 | |
| 877.0198 | 889.9431 | 905.6620 | 923.6817 | 927.6588 | 943.6340 | 1002.9798 |
| 1018.7167 | 1036.7046 | 1040.7238 | 1056.6945 | 1063.3297 | 1079.0752 | 1116.0163 |
| 1131.7560 | 1149.7860 | 1153.7654 | 1169.7402 | 1229.0710 | 1244.8292 | 1262.8523 |
| 1266.8593 | 1282.7904 | 1342.0994 | 1357.9284 | 1375.9517 | 1379.9293 | 1413.9492 |
| 1471.0408 | 1475.6861 | 1489.0704 | 1493.0714 | 1584.1187 | 1602.1516 | 1697.2401 |
| 1715.2577 | 1737.1939 | 1828.3534 | 1993.9914 | 2211.1000 | 2225.1434 | |

IEF spot 2408:

| | | | | | |
|---|---|---|---|---|---|
| 842.5100 | 1045.4988 | 1239.5138 | 1287.6241 | 1462.7030 | 1590.8423 | 1601.7867 |
| 1794.7912 | 1838.8872 | 1903.0143 | 1940.9054 | 1987.1174 | 1993.9468 | 2083.0461 |
| 2211.1000 | | | | | | |

IEF spot 2411:

| | | | | | |
|---|---|---|---|---|---|
| 842.5100 | 870.5059 | 895.4053 | 995.5448 | 1009.5518 | 1023.5688 | 1045.4862 |
| 1179.4954 | 1201.5783 | 1234.5657 | 1263.5824 | 1277.6078 | 1307.5765 | 1314.6757 |
| 1325.6195 | 1383.6090 | 1404.5953 | 1427.7396 | 1434.6573 | 1458.6092 | 1460.6883 |
| 1462.6815 | 1475.6602 | 1478.6293 | 1512.7909 | 1524.8316 | 1564.6905 | 1576.6922 |
| 1580.6980 | 1611.7268 | 1638.7754 | 1649.7423 | 1660.7930 | 1700.7628 | 1707.7236 |
| 1716.7952 | 1725.7846 | 1743.8049 | 1754.9104 | 1762.7919 | 1766.7505 | 1794.7743 |

TABLE 6-continued

HUMAN ISLET CELL PROTEINS CHARACTERISED BY MS
The peptide molecular weight values are read directly out of the mass spectrometer and are thus associated with the accuracies normally obtained with such instrumentation. These mass values are from human islet cell proteins recovered from the IEF gels and do not match any protein recorded in publicly available databases (whether nucleotide or protein sequence).

| | | | | | | |
|---|---|---|---|---|---|---|
| 1826.7847 | 1837.8701 | 1855.8577 | 1900.9779 | 1940.9038 | 1993.9091 | 2011.9112 |
| 2016.0210 | 2027.1124 | 2082.9987 | 2152.9815 | 2196.1547 | 2201.1245 | 2211.1000 |
| 2284.1674 | 2298.1775 | 2315.1778 | 2402.2727 | 2521.3566 | | |

IEF spot 13652:

| | | | | | | |
|---|---|---|---|---|---|---|
| 973.5179 | 1036.4774 | 1060.5342 | 1065.4002 | 1090.4578 | 1157.5122 | 1179.5299 |
| 1193.5473 | 1263.6227 | 1277.6329 | 1307.6100 | 1320.5257 | 1383.6186 | 1421.6125 |
| 1434.6909 | 1458.6522 | 1475.6960 | 1493.6697 | 1513.7133 | 1532.7183 | 1638.8153 |
| 1657.7778 | 1707.7530 | 1716.8296 | 1784.6837 | 1796.9843 | 1837.9545 | 1851.9192 |
| 1941.9522 | 1993.9786 | 2054.1177 | 2150.1636 | 2184.0966 | 2211.0999 | 2225.1274 |
| 2383.9529 | 2400.0149 | 2510.1564 | | | | |

IEF spot 14098:

| | | | | | | |
|---|---|---|---|---|---|---|
| 1151.6250 | 1187.5380 | 1211.6015 | 1252.6166 | 1263.6201 | 1267.6316 | 1277.6330 |
| 1302.6286 | 1307.6252 | 1329.6415 | 1340.5773 | 1383.6123 | 1424.6965 | 1460.7071 |
| 1475.6824 | 1487.7308 | 1535.8328 | 1555.7827 | 1589.7920 | 1613.8149 | 1638.8404 |
| 1647.7635 | 1663.3717 | 1700.9248 | 1707.7385 | 1716.8250 | 1743.8547 | 1778.9302 |
| 1794.7865 | 1837.9159 | 1851.9112 | 1872.9419 | 1881.0100 | 1922.9211 | 1933.9521 |
| 1940.9217 | 1964.9583 | 1987.0662 | 1993.9735 | 2035.0110 | 2082.9785 | 2184.1098 |
| 2196.1297 | 2211.0999 | 2225.1263 | 2230.1914 | 2239.1200 | 2250.0874 | 2314.1757 |

TABLE 7

HUMAN ISLET CELL PROTEINS CHARACTERISED BY MS
The peptide molecular weight values are read directly out of the mass spectrometer and are thus associated with the accuracies normally obtained with such instrumentation. These mass values are from human islet cell proteins recovered from the NEPHGE gels and do not match any protein recorded in publicly available databases (whether nucleotide or protein sequence).

NEPHGE spot 26:

| | | | | | | |
|---|---|---|---|---|---|---|
| 842.5131 | 870.5369 | 1045.5217 | 1179.5371 | 1265.5405 | 1277.6271 | 1308.5457 |
| 1314.6746 | 1320.5417 | 1324.5497 | 1357.6471 | 1427.7444 | 1475.6748 | 1493.6661 |
| 1664.8418 | 1703.9330 | 1716.7841 | 1719.8587 | 1743.8199 | 1760.7887 | 1775.8273 |
| 1791.7874 | 1794.7814 | 1826.7590 | 1940.8930 | 1945.9745 | 1993.9401 | 2211.0453 |
| 2225.0987 | 2230.1019 | 2239.1267 | 2284.1508 | 2299.1526 | 2314.0976 | 2383.8783 |

NEPHGE spot 35:

| | | | | | | |
|---|---|---|---|---|---|---|
| 1169.6652 | 1277.6525 | 1320.5251 | 1366.6936 | 1403.7316 | 1427.7965 | 1467.6493 |
| 1475.7490 | 1486.6881 | 1550.7053 | 1638.8392 | 1651.8001 | 1707.8210 | 1794.8089 |
| 1838.8934 | 1940.9146 | 1950.9534 | 1994.0184 | 2011.9465 | 2082.9935 | 2152.1050 |
| 2157.1118 | 2211.0999 | 2292.1087 | 2313.1264 | 2368.9793 | 2418.3266 | 2439.1478 |
| 2467.3066 | 2468.3029 | 2563.0697 | 2581.4875 | 2597.4212 | 2921.4292 | 3034.4707 |
| 3220.5008 | 3494.9136 | 3510.9276 | 3636.8963 | | | |

NEPHGE spot 60:

| | | | | | | |
|---|---|---|---|---|---|---|
| 842.5164 | 1277.6644 | 1302.6646 | 1360.5887 | 1383.6568 | 1385.7016 | 1393.6752 |
| 1401.7137 | 1438.8428 | 1475.7287 | 1553.7800 | 1624.9132 | 1638.9032 | 1662.9161 |
| 1667.8327 | 1707.8457 | 1716.8488 | 1747.9246 | 1751.9333 | 1774.9206 | 1794.8637 |
| 1816.8897 | 1837.9933 | 1841.0036 | 1851.9912 | 1941.0238 | 1994.0339 | 2150.1644 |
| 2211.1608 | | | | | | |

NEPHGE spot 76:

| | | | | | | |
|---|---|---|---|---|---|---|
| 1383.6718 | 1446.7509 | 1475.7966 | 1670.8364 | 1675.8901 | 1708.8213 | 1794.8184 |
| 1940.8887 | 1962.9070 | 1993.9970 | 2082.9848 | 2153.0730 | 2211.0999 | 2225.1123 |
| 2230.1870 | 2239.1271 | 2280.1950 | 2283.2022 | 2292.0475 | 2297.1802 | 2344.2374 |
| 2401.2168 | 2663.2692 | 2720.2978 | 2748.2944 | 2807.3426 | 2914.5394 | 2921.4777 |
| 3034.4733 | 3121.4973 | 3494.8696 | | | | |

NEPHGE spot 85:

| | | | | | | |
|---|---|---|---|---|---|---|
| 1045.5675 | 1106.4748 | 1179.5952 | 1195.5824 | 1277.6749 | 1308.6332 | 1320.5991 |
| 1350.6556 | 1475.7490 | 1574.8568 | 1638.8508 | 1649.8395 | 1657.8089 | 1687.9355 |
| 1707.7763 | 1716.8866 | 1794.8259 | 1813.8380 | 1838.9120 | 1901.0576 | 1940.9125 |
| 1993.9837 | 2016.0573 | 2024.0827 | 2083.9875 | 2121.0337 | 2153.0677 | 2211.1000 |
| 2298.1652 | | | | | | |

TABLE 7-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the NEPHGE gels
and do not match any protein recorded in publicly available databases (whether
nucleotide or protein sequence).

NEPHGE spot 128:

| | | | | | |
|---|---|---|---|---|---|
| 842.5173 | 950.6940 | 985.5799 | 1011.6137 | 1033.7815 | 1045.5060 | 1068.6652 |
| 1077.7487 | 1179.5300 | 1211.6160 | 1277.6031 | 1299.8620 | 1307.6073 | 1334.7733 |
| 1335.7890 | 1338.7442 | 1341.9049 | 1370.7179 | 1376.8093 | 1425.0543 | 1434.6812 |
| 1541.0283 | 1665.9233 | 1691.1798 | 1726.0926 | 1727.1155 | 1761.0134 | 2211.0275 |

NEPHGE spot 130:

| | | | | | |
|---|---|---|---|---|---|
| 1045.5140 | 1179.5478 | 1193.5777 | 1277.6468 | 1307.6332 | 1338.7790 | 1365.5711 |
| 1383.6908 | 1389.6799 | 1434.7248 | 1475.7414 | 1493.7520 | 1535.8696 | 1666.0050 |
| 1707.8047 | 1716.9037 | 1743.9190 | 1794.8584 | 1838.0415 | 1994.0216 | 2035.0458 |
| 2211.1738 | | | | | | |

NEPHGE spot 171:

| | | | | | |
|---|---|---|---|---|---|
| 908.7717 | 942.7243 | 944.7402 | 950.8137 | 1033.8325 | 1045.6096 | 1060.5907 |
| 1157.5914 | 1165.5494 | 1179.6000 | 1201.6932 | 1232.5837 | 1235.5335 | 1277.7091 |
| 1291.6390 | 1299.9770 | 1308.6576 | 1327.7262 | 1333.9192 | 1335.9331 | 1342.0107 |
| 1370.6904 | 1393.7220 | 1444.8475 | 1461.7450 | 1475.7837 | 1493.7477 | 1533.7963 |
| 1567.8593 | 1581.7525 | 1586.7939 | 1599.8235 | 1605.8154 | 1616.8242 | 1629.8415 |
| 1657.8337 | 1682.8824 | 1691.2433 | 1707.8322 | 1714.8844 | 1716.8714 | 1741.7966 |
| 1744.9603 | 1752.8348 | 1791.7680 | 2099.0363 | 2211.0999 | | |

NEPHGE spots 187 and 188:

| | | | | | |
|---|---|---|---|---|---|
| 1123.5817 | 1251.7002 | 1292.6499 | 1403.7788 | 1448.7823 | 1508.7700 | 1576.8817 |
| 1638.9820 | 1687.9971 | 1780.0016 | 1908.0271 | 2002.1204 | 2182.3150 | 2199.3031 |
| 2211.2807 | 2225.2657 | 2230.3124 | 2283.2795 | 2295.3212 | 2587.5794 | 2662.7369 |
| 2705.3950 | 2720.5340 | 2748.5163 | | | | |

NEPHGE spot 195:

| | | | | | |
|---|---|---|---|---|---|
| 973.5609 | 976.5443 | 1045.5840 | 1157.5838 | 1179.5999 | 1201.6708 | 1234.6620 |
| 1263.6625 | 1277.7208 | 1284.6043 | 1300.5175 | 1307.6708 | 1320.5245 | 1323.6305 |
| 1337.6572 | 1357.6867 | 1365.6012 | 1383.7097 | 1386.6658 | 1434.7588 | 1475.7479 |
| 1493.7223 | 1638.8590 | 1707.7833 | 1716.8781 | 1755.8142 | 1794.7931 | 1837.9626 |
| 1851.9484 | 1882.0046 | 1890.9783 | 1905.0450 | 1940.9194 | 1993.9950 | 2083.0237 |
| 2211.0999 | | | | | | |

NEPHGE spot 243:

| | | | | | |
|---|---|---|---|---|---|
| 1045.5466 | 1060.0443 | 1066.0453 | 1794.7869 | 2211.1470 | 2225.1316 | 2236.2563 |
| 2239.2134 | | | | | | |

NEPHGE spot 270:

| | | | | | |
|---|---|---|---|---|---|
| 950.7789 | 973.5897 | 989.5751 | 1003.5955 | 1025.6590 | 1029.6033 | 1036.5737 |
| 1045.5866 | 1060.5666 | 1064.6402 | 1074.5264 | 1082.5967 | 1090.5566 | 1107.5747 |
| 1157.5786 | 1165.5700 | 1179.6000 | 1201.6640 | 1213.6248 | 1232.6071 | 1234.6742 |
| 1257.6697 | 1259.6823 | 1263.6743 | 1277.7118 | 1299.9629 | 1300.5490 | 1307.6720 |
| 1323.6470 | 1335.9371 | 1357.7143 | 1379.7259 | 1383.6952 | 1393.7250 | 1404.7544 |
| 1407.6986 | 1434.7663 | 1438.7044 | 1475.7611 | 1493.7269 | 1504.8006 | 1523.8004 |
| 1560.8202 | 1638.9009 | 1657.7832 | 1691.2608 | 1707.7958 | 1716.8609 | 1791.7356 |
| 1793.9708 | 1795.8320 | 1837.9885 | 1851.9594 | 1890.9722 | 1940.9413 | 1993.9967 |
| 2054.1412 | 2064.1473 | 2086.0239 | 2120.0246 | 2211.0999 | 2509.1782 | |

NEPHGE spot 421:

| | | | | | |
|---|---|---|---|---|---|
| 1045.5551 | 1140.6401 | 1179.5911 | 1201.6178 | 1218.6234 | 1233.6811 | 1277.6552 |
| 1302.6608 | 1307.6456 | 1314.7202 | 1454.6592 | 1475.7489 | 1535.8938 | 1560.7882 |
| 1567.8222 | 1628.7809 | 1660.8150 | 1664.9552 | 1716.8609 | 1784.9210 | 1793.1088 |
| 1913.0411 | 1940.9146 | 1963.9912 | 1993.9933 | 2211.0999 | | |

NEPHGE spot 449:

| | | | | | |
|---|---|---|---|---|---|
| 1775.7252 | 2210.8860 | 2224.9665 | 2238.8424 | 2663.1016 | 2720.1628 | 2749.1314 |
| 2807.1013 | 2821.1104 | 3121.5130 | | | | |

NEPHGE spot 508:

| | | | | | |
|---|---|---|---|---|---|
| 842.5100 | 1045.5536 | 1066.5542 | 1179.5953 | 1183.6831 | 1236.5941 | 1291.6831 |
| 1295.6332 | 1307.6875 | 1403.6576 | 1428.8009 | 1475.7001 | 1665.6731 | 1763.8092 |
| 1784.9099 | 1794.8168 | 1801.9166 | 1816.9433 | 1993.9722 | 2052.1099 | 2072.1142 |
| 2140.0546 | 2180.2004 | 2211.0999 | 2225.1141 | 2230.1947 | 2239.1373 | 2246.1973 |
| 2283.1010 | 2292.0967 | 2299.1391 | 2313.1951 | 2344.1912 | 2361.2462 | 2663.3861 |
| 2678.1476 | 2720.3396 | 2748.1750 | 2807.3801 | 2821.3286 | 3121.6227 | 3339.9020 |
| 3349.7006 | | | | | | |

TABLE 7-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the NEPHGE gels
and do not match any protein recorded in publicly available databases (whether
nucleotide or protein sequence).

NEPHGE spot 509:

| | | | | | | |
|---|---|---|---|---|---|---|
| 842.5661 | 950.7645 | 1045.5750 | 1138.4976 | 1141.5052 | 1157.5242 | 1162.5323 |
| 1179.5556 | 1188.6617 | 1192.5322 | 1201.6627 | 1206.5864 | 1207.5732 | 1231.5848 |
| 1248.5986 | 1254.5988 | 1264.6176 | 1277.6566 | 1299.9226 | 1308.6124 | 1309.6189 |
| 1314.7051 | 1335.8741 | 1341.9762 | 1351.6377 | 1369.6827 | 1408.7250 | 1431.6785 |
| 1440.6923 | 1475.7310 | 1548.7768 | 1562.7803 | 1582.8090 | 1621.9304 | 1691.2267 |
| 1716.8358 | 1725.1946 | 1727.1917 | 1749.9958 | 1794.8245 | 1990.0044 | 2006.0106 |
| 2034.9689 | 2211.1000 | 2398.2911 | 2672.2803 | 3530.7912 | | |

NEPHGE spot 532:

| | | | | | | |
|---|---|---|---|---|---|---|
| 842.5100 | 856.5163 | 987.4343 | 998.4821 | 1012.4873 | 1045.5354 | 1066.5093 |
| 1078.4847 | 1080.5039 | 1092.4997 | 1100.5099 | 1665.7157 | 1679.7342 | 1691.7426 |
| 1697.7075 | 1707.7815 | 1794.8100 | 1826.7846 | 1846.8073 | 1940.9527 | 2011.9847 |
| 2078.1252 | 2082.9893 | 2211.0999 | 2225.0967 | 2239.1366 | 2283.1418 | 2297.1983 |
| 2313.2183 | 2344.2588 | 2663.3824 | 2691.3461 | 2705.3164 | 2720.3205 | 2734.3788 |
| 2744.3915 | 2748.3478 | 2807.3461 | 2821.4211 | 2914.6472 | 2921.3275 | 3338.9020 |
| 3348.7397 | | | | | | |

NEPHGE spot 558:

| | | | | | | |
|---|---|---|---|---|---|---|
| 831.5173 | 908.6378 | 944.5866 | 950.6773 | 973.4943 | 1003.4784 | 1027.4818 |
| 1031.5106 | 1033.4303 | 1037.4838 | 1045.4983 | 1090.4512 | 1118.4363 | 1157.5146 |
| 1165.4922 | 1179.5187 | 1193.5475 | 1201.5905 | 1232.5216 | 1234.6120 | 1254.6082 |
| 1277.6373 | 1300.4872 | 1302.6032 | 1308.5774 | 1320.5401 | 1340.5812 | 1357.6289 |
| 1365.5703 | 1383.6340 | 1393.6433 | 1418.6599 | 1434.6912 | 1443.7196 | 1454.6651 |
| 1475.7090 | 1493.6847 | 1560.7731 | 1608.7220 | 1657.7727 | 1707.7505 | 1716.8222 |
| 1791.7034 | 1794.7971 | 1838.9112 | 2138.1215 | 2211.1154 | 2533.4148 | |

NEPHGE spot 560:

| | | | | |
|---|---|---|---|---|
| 1678.8305 | 1700.8144 | 1732.7947 | 1760.8185 | 2211.1243 |

NEPHGE spot 609:

| | | | | | | |
|---|---|---|---|---|---|---|
| 842.5823 | 1045.6003 | 1074.5479 | 1111.6290 | 1179.6000 | 1232.5793 | 1307.6391 |
| 1320.5689 | 1350.6723 | 1385.7186 | 1475.7164 | 1479.7159 | 1493.7217 | 1503.7389 |
| 1548.8342 | 1573.7621 | 1638.8672 | 1650.9216 | 1657.8110 | 1707.7865 | 1743.8224 |
| 1791.7538 | 1794.7899 | 1813.9147 | 1826.8037 | 1838.9318 | 1851.9457 | 1867.9339 |
| 1994.0167 | 2091.9105 | 2150.1387 | 2198.9669 | 2211.1000 | 2383.9361 | 2501.2078 |
| 2717.0710 | | | | | | |

NEPHGE spot 719:

| | | | | | | |
|---|---|---|---|---|---|---|
| 1245.4899 | 1256.5258 | 1273.5880 | 1600.6902 | 1738.8842 | 1743.7380 | 1794.7060 |
| 2034.7818 | 2210.8631 | 2282.9633 | 2541.9943 | 2637.0529 | 2662.1501 | 2719.9902 |
| 2780.1056 | | | | | | |

NEPHGE spot 729:

| | | | | | | |
|---|---|---|---|---|---|---|
| 842.6014 | 973.5732 | 995.6290 | 997.6764 | 1009.6652 | 1011.6854 | 1037.5903 |
| 1045.5939 | 1060.6033 | 1140.5753 | 1157.5940 | 1165.6028 | 1179.6000 | 1234.6787 |
| 1263.6654 | 1277.7022 | 1300.5221 | 1307.6667 | 1314.7520 | 1320.5957 | 1323.6536 |
| 1357.6990 | 1379.7386 | 1383.6807 | 1427.8123 | 1434.7499 | 1475.7565 | 1487.7571 |
| 1493.7502 | 1638.8667 | 1699.8308 | 1707.7936 | 1716.8692 | 1784.7536 | 1794.8321 |
| 1837.9871 | 1851.9540 | 1993.9841 | 2211.0999 | | | |

NEPHGE spot 829:

| | | | | | | |
|---|---|---|---|---|---|---|
| 728.6920 | 754.5651 | 806.5817 | 840.6673 | 901.6037 | 908.7999 | |
| 922.8081 | 929.5580 | 942.7504 | 944.7633 | 950.8350 | 984.6868 | 1045.6162 |
| 1060.5888 | 1065.5604 | 1069.5700 | 1101.6517 | 1107.5696 | 1115.5327 | 1168.6149 |
| 1175.6590 | 1179.6000 | 1191.6387 | 1201.6858 | 1204.6558 | 1234.6775 | 1264.5820 |
| 1277.7048 | 1289.6860 | 1297.7003 | 1307.6572 | 1314.7802 | 1335.9463 | 1344.7647 |
| 1357.7094 | 1383.6713 | 1475.7766 | 1599.8000 | 1641.7130 | 1716.8676 | 1743.8138 |
| 1759.8716 | 1761.8461 | 1763.9059 | 1778.9217 | 1785.9446 | 1794.8405 | 2211.0999 |
| 3553.7439 | | | | | | |

NEPHGE spot 836:

| | | | | | | |
|---|---|---|---|---|---|---|
| 550.6338 | 559.4159 | 594.3097 | 620.3219 | 628.2701 | 634.3534 | |
| 677.3904 | 705.4059 | 719.4081 | 763.4069 | 777.3504 | 816.4305 | |
| 842.5100 | 856.5303 | 870.5226 | 901.4988 | 944.5088 | 953.5746 | |
| 967.5807 | 979.4747 | 985.5182 | 1020.4115 | 1032.5642 | 1045.5452 | 1060.5229 |
| 1088.5526 | 1107.5244 | 1126.4778 | 1137.4690 | 1151.4924 | 1168.5205 | 1179.5371 |
| 1217.5778 | 1265.5486 | 1277.6444 | 1308.6107 | 1314.6961 | 1320.5574 | 1323.6041 |
| 1334.6886 | 1349.7357 | 1369.6180 | 1377.7381 | 1404.5148 | 1411.6379 | 1475.7199 |
| 1493.7304 | 1504.8048 | 1664.9080 | 1703.9596 | 1719.9754 | 1733.9201 | 1736.0145 |
| 1743.7900 | 1759.7683 | 1775.8072 | 1791.8303 | 1794.8143 | 1806.8917 | 1826.8090 |

TABLE 7-continued

HUMAN ISLET CELL PROTEINS CHARACTERISED BY MS
The peptide molecular weight values are read directly out of the mass spectrometer and
are thus associated with the accuracies normally obtained with such instrumentation.
These mass values are from human islet cell proteins recovered from the NEPHGE gels
and do not match any protein recorded in publicly available databases (whether
nucleotide or protein sequence).

| | | | | | | |
|---|---|---|---|---|---|---|
| 1831.7637 | 1837.9212 | 1853.9619 | 1858.9394 | 1906.9335 | 1945.9915 | 1993.9626 |
| 2113.0476 | 2117.9938 | 2123.1281 | 2128.0641 | 2211.1000 | 2221.1253 | 2225.1040 |
| 2240.1259 | 2283.1314 | 2292.0664 | 2299.1709 | 2314.1811 | 2383.9977 | |

NEPHGE spot 837:

| | | | | | | |
|---|---|---|---|---|---|---|
| 842.5100 | 944.5317 | 1020.4700 | 1055.5366 | 1242.5797 | 1281.5708 | 1362.6911 |
| 1625.7170 | 1763.7852 | 1794.7933 | 2152.9836 | 2211.1000 | 3173.9268 | |

NEPHGE spot 3879:

| | | | | | | |
|---|---|---|---|---|---|---|
| 806.4919 | 1029.6369 | 1036.5549 | 1045.5927 | 1065.5397 | 1087.5387 | 1090.5970 |
| 1115.5180 | 1157.6195 | 1165.5772 | 1175.6512 | 1179.6000 | 1198.6571 | 1201.6794 |
| 1205.6320 | 1232.6643 | 1243.6040 | 1277.7034 | 1297.6864 | 1300.5622 | 1307.6610 |
| 1314.7621 | 1320.5558 | 1323.6573 | 1330.7207 | 1337.6185 | 1340.7602 | 1344.7320 |
| 1383.6828 | 1426.7184 | 1434.7529 | 1438.8223 | 1441.7131 | 1469.7683 | 1475.7527 |
| 1493.7449 | 1535.8745 | 1634.8796 | 1638.8827 | 1656.7456 | 1675.8037 | 1707.7860 |
| 1716.8731 | 1728.8562 | 1743.8410 | 1759.8798 | 1785.9333 | 1794.8294 | 1804.8441 |
| 1838.9205 | 1990.1067 | 1994.0040 | 2211.1000 | | | |

NEPHGE spot 6600:

| | | | | | | |
|---|---|---|---|---|---|---|
| 1112.7125 | 1119.8876 | 1154.7604 | 1179.5853 | 1258.5560 | 1299.9739 | 1334.8759 |
| 1342.0311 | 1369.7625 | 1376.9353 | 1404.6771 | 1411.8281 | 1691.3292 | 1726.2245 |
| 1761.1320 | 1794.8996 | 2101.1599 | 2117.5243 | 2211.2240 | | |

TABLE 8

PROTEINS DETECTED IN HUMAN ISLET CELL MEDIA AND CHARACTERISED BY MS
The peptide molecular weight values are read directly out of the mass spectrometer and
are thus associated with the accuracy normally obtained with such instrumentation. These
mass values are from proteins detected in the media following incubation of human islets
in growth media (as described in the methods). The proteins are recovered from the IEF
gels. Their peptide mass values do not match to the peptides which would be generated if
any protein, recorded in publicly available databases (whether nucleotide or protein
sequence), was treated in a similar manner.

IEF spot 122SPI:

| | | | | | | |
|---|---|---|---|---|---|---|
| 842.5100 | 927.4963 | 973.5343 | 1066.4649 | 1109.4248 | 1165.5350 | 1179.5583 |
| 1213.6268 | 1234.6228 | 1263.6294 | 1277.6595 | 1300.4708 | 1307.6346 | 1315.6246 |
| 1320.5471 | 1357.6533 | 1365.5835 | 1379.6918 | 1383.6430 | 1390.6393 | 1400.6369 |
| 1405.6680 | 1421.6233 | 1427.7104 | 1434.7311 | 1475.7333 | 1493.6983 | 1497.7529 |
| 1513.7643 | 1639.9035 | 1657.7697 | 1699.8245 | 1707.7840 | 1716.8404 | 1745.8399 |
| 1797.0431 | 1819.0044 | 1834.9854 | 1837.9651 | 1993.9989 | 2096.1253 | 2114.1074 |
| 2129.9106 | 2211.0999 | 2224.2375 | 2239.1053 | 2249.0984 | 2367.2937 | 2383.9584 |
| 2509.2311 | 2705.2275 | 2872.5248 | 3314.3928 | | | |

IEF spot 123SPI:

| | | | | | | |
|---|---|---|---|---|---|---|
| 842.5100 | 995.6139 | 1045.5020 | 1179.5325 | 1257.6289 | 1277.6396 | 1307.6108 | 1382.6104 |
| 1418.6783 | 1434.7291 | 1475.7101 | 1487.7178 | 1523.7513 | 1540.7742 | 1604.7757 | 1608.7595 |
| 1638.8370 | 1707.7398 | 1716.8473 | 1794.8201 | 1812.0723 | 1837.9388 | 1851.9256 | 1867.9182 |
| 1901.0100 | 1940.9715 | 1993.9586 | 2113.0096 | 2150.0818 | 2184.0996 | 2211.0999 | 2225.1103 |
| 2231.1825 | 2345.2339 | 2384.9304 | | | | | |

IEF spot 126SPI:

| | | | | | | |
|---|---|---|---|---|---|---|
| 842.5100 | 1023.6778 | 1095.6006 | 1137.7430 | 1164.6686 | 1198.6274 | 1204.6551 | 1217.6581 |
| 1277.6826 | 1291.6875 | 1308.6616 | 1313.6816 | 1366.7194 | 1371.7416 | 1383.6704 | 1428.7966 |
| 1439.7924 | 1444.7147 | 1475.7456 | 1487.7390 | 1570.8290 | 1619.8479 | 1629.8740 | 1638.8514 |
| 1662.8514 | 1674.8398 | 1679.8136 | 1684.8887 | 1692.8810 | 1707.7897 | 1794.8050 | 1824.9642 |
| 1837.9740 | 1852.9313 | 1867.9291 | 1869.9953 | 1896.0050 | 1902.0257 | 1940.9322 | 1953.0459 |
| 1962.9743 | 1993.9616 | 2151.0562 | 2158.1156 | 2169.0372 | 2184.0868 | 2211.1000 | 2283.2157 |
| 2297.1638 | 2345.2835 | 2748.3837 | | | | | |

IEF spot 130SPI:

| | | | | | | |
|---|---|---|---|---|---|---|
| 842.5100 | 1036.5147 | 1075.5384 | 1082.5560 | 1107.5100 | 1165.5090 | 1179.5516 | 1198.6566 |
| 1277.6451 | 1303.6580 | 1307.6217 | 1329.6573 | 1393.6412 | 1455.6351 | 1475.7144 | 1487.7050 |
| 1515.7538 | 1638.8218 | 1657.7565 | 1704.8650 | 1707.7353 | 1758.8640 | 1790.8768 | 1794.7723 |
| 1799.8790 | 1811.8747 | 1837.9550 | 1839.9159 | 1872.9456 | 1914.0100 | 1941.9548 | 1993.9509 |
| 2047.0529 | 2054.0744 | 2150.0295 | 2184.0963 | 2211.0999 | 2250.0364 | 2383.9437 | |

TABLE 8-continued

PROTEINS DETECTED IN HUMAN ISLET CELL MEDIA AND CHARACTERISED BY MS
The peptide molecular weight values are read directly out of the mass spectrometer and
are thus associated with the accuracy normally obtained with such instrumentation. These
mass values are from proteins detected in the media following incubation of human islets
in growth media (as described in the methods). The proteins are recovered from the IEF
gels. Their peptide mass values do not match to the peptides which would be generated if
any protein, recorded in publicly available databases (whether nucleotide or protein
sequence), was treated in a similar manner.

IEF spot 135SPI:

| | | | | | | | |
|---|---|---|---|---|---|---|---|
| 842.5100 | 1271.6481 | 1343.6065 | 1413.7382 | 1440.6092 | 1452.6148 | 1515.7276 | 1571.7985 |
| 1692.8303 | 1709.7921 | 1794.8135 | 2211.1000 | | | | |

IEF spot 140SPI:

| | | | | | | | |
|---|---|---|---|---|---|---|---|
| 842.5100 | 995.6118 | 1192.5588 | 1198.6323 | 1277.6308 | 1311.5802 | 1333.6658 | 1344.5990 |
| 1350.6185 | 1419.6963 | 1475.7224 | 1487.6666 | 1515.7236 | 1575.7435 | 1638.8524 | 1687.8674 |
| 1707.7437 | 1773.8513 | 1780.8198 | 1790.8845 | 1794.8104 | 1838.9057 | 1853.9362 | 1858.9484 |
| 1901.1178 | 1954.0130 | 1993.9445 | 2016.0588 | 2075.9670 | 2155.1313 | 2211.0999 | 2279.2190 |
| 2284.2035 | 2384.9802 | 2401.1453 | | | | | |

IEF spot 160SPI:

| | | | | | | | |
|---|---|---|---|---|---|---|---|
| 842.5100 | 944.4201 | 1045.4319 | 1093.3863 | 1121.4125 | 1179.4628 | 1195.4396 | 1277.5655 |
| 1297.5044 | 1302.5312 | 1307.5412 | 1320.4609 | 1350.5468 | 1383.5719 | 1475.6543 | 1556.6594 |
| 1638.8052 | 1650.7700 | 1657.7602 | 1684.7837 | 1707.7410 | 1794.7624 | 1812.8635 | 1838.9208 |
| 1851.8857 | 1872.9481 | 1931.9711 | 1993.9814 | 2211.0999 | 2225.1307 | 2383.9509 | 2389.2171 |

IEF spot 218SPI:

| | | | | | | |
|---|---|---|---|---|---|---|
| 842.5100 | 950.6771 | 995.4745 | 1021.4311 | 1043.4929 | 1045.4833 | 1060.5128 |
| 1109.4391 | 1126.4305 | 1142.4871 | 1157.5613 | 1179.5079 | 1199.4923 | 1210.5203 |
| 1220.5043 | 1234.6055 | 1263.6086 | 1277.6299 | 1286.5597 | 1300.4350 | 1302.6175 |
| 1307.5960 | 1314.7119 | 1320.5066 | 1329.5849 | 1353.6598 | 1357.6076 | 1365.5460 |
| 1383.5880 | 1393.6262 | 1427.7609 | 1434.7341 | 1475.6921 | 1493.6654 | 1545.7737 |
| 1553.7960 | 1700.7823 | 1707.7831 | 1714.8079 | 1716.8088 | 1726.8174 | 1794.7979 |
| 1825.9672 | 1838.9224 | 1922.9490 | 1933.9836 | 1940.9304 | 1987.0506 | 1993.9688 |
| 2005.0097 | 2083.0669 | 2211.0999 | 2225.1217 | 2230.1991 | 2239.1338 | 2283.2517 |
| 2297.1804 | 2344.3708 | 2367.2739 | 2384.1822 | 2401.2136 | 2662.6332 | 3077.6726 |
| 3095.4811 | 3339.9445 | 3349.7509 | | | | |

IEF spot 248SPI:

| | | | | | | | |
|---|---|---|---|---|---|---|---|
| 842.5100 | 995.5661 | 1192.5533 | 1198.6455 | 1344.5956 | 1419.6789 | 1424.7739 | 1515.7473 |
| 1704.8844 | 1794.8113 | 1869.9654 | 1902.0689 | 1940.9132 | 1952.9542 | 1959.9920 | 2016.1083 |
| 2153.1172 | 2155.0712 | 2211.1000 | 2279.1779 | 2284.1800 | 2344.2439 | 2402.2584 | |

IEF spot 277SPI:

| | | | | | | | |
|---|---|---|---|---|---|---|---|
| 842.5100 | 944.5108 | 989.5777 | 1032.5590 | 1137.6793 | 1180.5632 | 1277.6210 | 1325.6529 |
| 1335.6512 | 1349.6238 | 1363.6523 | 1366.7033 | 1398.7028 | 1467.7336 | 1475.7235 | 1538.8441 |
| 1602.7634 | 1636.8005 | 1638.8129 | 1652.7675 | 1670.9066 | 1703.8669 | 1719.9301 | 1743.8032 |
| 1758.8949 | 1794.7991 | 1839.8938 | 1931.1572 | 1940.9432 | 1993.9414 | 2030.0920 | 2153.0395 |
| 2176.9849 | 2211.0999 | 2284.1637 | 2298.1739 | 2345.2744 | | | |

IEF spot 304SPI:

| | | | | |
|---|---|---|---|---|
| 842.7320 | 2211.6199 | 2225.6395 | 2284.7376 | 2346.7681 |

IEF spot 314SPI:

| | | | | | | | |
|---|---|---|---|---|---|---|---|
| 1747.1466 | 1929.2249 | 2040.3318 | 2079.2340 | 2292.4766 | 2309.5383 | 2338.5453 | 2367.6507 |

IEF spot 338SPI:

| | | | | | | | |
|---|---|---|---|---|---|---|---|
| 842.5100 | 1277.6344 | 1298.6552 | 1302.6274 | 1307.5972 | 1329.6478 | 1381.7755 | 1398.6603 |
| 1426.7642 | 1475.7128 | 1487.6784 | 1523.7645 | 1602.7505 | 1638.8279 | 1707.7565 | 1742.8419 |
| 1758.8799 | 1784.7091 | 1794.7915 | 1812.0358 | 1838.9245 | 1851.9135 | 1867.8992 | 1941.9594 |
| 1966.0151 | 1969.0193 | 1993.9537 | 2150.0574 | 2176.0349 | 2184.0894 | 2211.0999 | 2225.1184 |
| 2286.1485 | 2299.1497 | 2331.1452 | 2361.1860 | 2383.9924 | 2501.1805 | 2509.2701 | 2580.3195 |
| 2643.3333 | 2702.2667 | 2707.2342 | 2718.2130 | 2723.3186 | 2808.3617 | 2832.3462 | |

The invention claimed is:

1. A method for diagnosing diabetes in a mammal, the method comprising determining in a pancreas sample the level of expression of at least one marker protein selected from the group consisting of:
   a) P05451 (known as islet cell regeneration factor; lithostathine 1 alpha, pancreatic stone protein; and pancreatic thread protein);
   b) P 19971 (known as thymidine phosphorylase; platelet derived endothelial cell growth factor; and gliostatin);
   c) P30740 (known as leukocyte elastase inhibitor); and
   d) P80188 (known as alpha 2 microglobulin related subunit of MMP and lipocalin-2),
   wherein increased expression of a), b), c) and/or d) indicates that the mammal has diabetes.

2. The method according to claim 1, wherein the mammal is a human.

3. A method for determining the predisposition for diabetes in a mammal, the method comprising determining in a pancreas sample the level of expression of at least one marker protein selected from the group consisting of:
- a) P05451 (known as islet cell regeneration factor; lithostathine 1 alpha, pancreatic stone protein; and pancreatic thread protein);
- b) P19971 (known as thymidine phosphorylase; platelet derived endothelial cell growth factor; and gliostatin),
- c) P30740 (known as leukocyte elastase inhibitor); and
- d) PS0188 (known as alpha 2 microglobulin related subunit of MMP and lipocalin-2),
- wherein increased expression of a), b), c) and/or d) indicates that the mammal has a predisposition for diabetes.

4. A method for determining the predisposition in a human for diabetes, the method comprising:
- i) determining in a pancreas sample originating form the human the increased expression of at least one marker protein selected from the group consisting of:
  - a) P05451 (known as islet cell regeneration factor; lithostathine 1 alpha, pancreatic stone protein; and pancreatic thread protein);
  - b) P19971 (known as thymidine phosphorylase; platelet derived endothelial cell growth factor; and gliostatin);
  - c) P30740 (known as leukocyte elastase inhibitor); and
  - d) P80188 (known as alpha 2 microglobulin related subunit of MMP and lipocalin-2),
  - wherein increased expression of a), b), c) and/or d) indicates that the mammal has a predisposition for diabetes;
- ii) determining in a pancreas sample originating form the human the decreased expression of at least one marker protein selected from the group consisting of:
  - a) P05451 (known as islet cell regeneration factor; lithostathine 1 alpha, pancreatic stone protein; and pancreatic thread protein);
  - b) P 19971 (known as thymidine phosphorylase; platelet derived endothelial cell growth factor; and gliostatin);
  - c) P30740 (known as leukocyte elastase inhibitor); and
  - d) P80188 (known as alpha 2 microglobulin related subunit of MMP and lipocalin-2),
  - wherein decreased expression of a), b), c) and/or d) indicates that the mammal has a reduced predisposition for diabetes.

* * * * *